(12) United States Patent
Ogawa et al.

(10) Patent No.: US 8,097,770 B2
(45) Date of Patent: Jan. 17, 2012

(54) PLANT HAVING IMPROVED GROWTH ABILITY AND DISEASE RESISTANCE AND METHOD FOR PRODUCTION THEREOF

(75) Inventors: Kenichi Ogawa, Okayama (JP); Masayoshi Matsumoto, Okayama (JP); Tomonori Shiraishi, Okayama (JP)

(73) Assignees: Japan Science and Technology, Saitama (JP); Okayama Prefecture, Okayama (JP)

(*) Notice: Subject to any disclaimer, the term of this patent is extended or adjusted under 35 U.S.C. 154(b) by 411 days.

(21) Appl. No.: 12/278,778

(22) PCT Filed: Feb. 8, 2007

(86) PCT No.: PCT/JP2007/052216
§ 371 (c)(1),
(2), (4) Date: Jun. 16, 2009

(87) PCT Pub. No.: WO2007/091634
PCT Pub. Date: Aug. 16, 2007

(65) Prior Publication Data
US 2009/0300797 A1 Dec. 3, 2009

(30) Foreign Application Priority Data
Feb. 9, 2006 (JP) .................................. 2006-032895

(51) Int. Cl.
*A01H 1/00* (2006.01)
*A01H 5/00* (2006.01)
*C12N 5/14* (2006.01)

(52) U.S. Cl. ........ 800/278; 800/279; 800/290; 800/298; 800/301; 800/302; 435/410

(58) Field of Classification Search .................. 800/278, 800/290
See application file for complete search history.

(56) References Cited

U.S. PATENT DOCUMENTS

| 6,441,277 B1 * | 8/2002 | Barry et al. ................... 800/298 |
| 2004/0034888 A1 | 2/2004 | Liu et al. |

FOREIGN PATENT DOCUMENTS

| EP | 1033405 | * | 9/2000 |
| EP | 1033405 A2 | | 9/2000 |
| JP | 2003-088379 | | 3/2003 |
| JP | 2005-192496 | | 7/2005 |
| WO | WO-02/16655 A2 | | 2/2002 |
| WO | WO-2004/061080 A | | 7/2004 |

OTHER PUBLICATIONS

Berrocal-Lobo, M. et al. (2002). "Constitutive Expression of Ethylene-Response-Factor1 in *Arabidopsis* Confers Resistance to Several Necrotrophic Fungi," *The Plant Journal* 29(1):23-32.
Haake, V. et al. (1998). "A Moderate Decrease of Plastid Aldolase Activity Inhibits Photosynthesis, Alters the Levels of Sugars and Starch, and Inhibits Growth of Potato Plants," *The Plant Journal* 14(2):147-157.

International Search Report mailed Apr. 3, 2007, for PCT Application No. PCT/JP2007/052216 filed Feb. 8, 2007, 5 pages.
Ito, H. et al. (2003). "The Sugar-Metabolic Enzymes Aldolase and Triose-Phosphate Isomerase are Targets of Glutathionylation in *Arabidopsis thaliana*: Detection Using Biotinylated Glutathione," *Plant & Cell Physiology* 44(7):655-660.
Kasuga, M. et al. (Mar. 1999). "Improving Plant Drought, Salt, and Freezing Tolerance by Gene Transfer of a Single Stress-inducible Transcription Factor," *Nature Biotechnology* 17:287-291.
Matsumoto, M. et al. (2004). "Redox Regulation of Chloroplast-type Aldolase by Glutathione in *Arabidopsis*," *Plant & Cell Physiology* 45(Supplement):s153, Abstract 503(3pA11).
Matsumoto, M. et al. (2005). "Characterization of Chloroplastic Fructose-1,6-Bisphosphate Aldolase of Arabiodopsis," *Plant & Cell Physiology* 46(Supplement):s171, Abstract 587(PA260).
Matsumoto, M. et al. (Aug. 4, 2005). "Different Features Concerning Redox Control of Plastidic Aldolast Isozymes of Arabidopsis," *Summaries of 23rd Kyoto Annual Meeting and Symposium of Japanese Society for Plant Cell and Molecular Biology Preparatory Commitee*, p. 140, Abstract 2Da2. (English Translation attached, 2 pages).
Miyagawa, Y. et al. (Oct. 2001). "Overexpression of a Cyanobacterial Fructose-1,6-/Sedoheptulose-1,7-Bisphosphatase in Tobacco Enhances Photosynthesis and Growth," *Nature Biotechnology* 19:965-969.
Ogawa, K. et al. (2005). "Fructose-1,6-Bisphosphate Aldolase is a Target Protein of Glutathionylation in Arabidopsis Chloroplasts," *Photosynthesis: Fundamental Aspects to Global Perspectives*, pp. 468-470.
Ogawa, K. et al. (Aug. 30, 2004). "Fructose-1,6-Bisphosphate Aldolase is a Target Protein of Glutathionylation in Arabidopsis Chloroplasts," 13th International Congress on Photosynthesis, Symposium S1B Photooxidative Stress, Photoinhibition, Montreal, Quebec, Canada, 1 page.
Tang, X. et al. (Jan. 1999). "Overexpression of *Pto* Activates Defense Responses and Confers Broad Resistance," *The Plant Cell* 11:15-29.
Yanagisawa, S. et al. (May 18, 2004). "Metabolic Engineering with Dof1 Transcription Factor in Plants: Improved Nitrogen Assimilation and Growth Under Low-Nitrogen Conditions," *Proceedings of the National Academy of Sciences of the United States of America* 101(20):7833-7838.
European Search Report and Written Opinion mailed Aug. 17, 2009, for EP Application No. 07713932.7 filed Sep. 9, 2008, 6 pages.
GH, H.S. et al. (2002). "Proteomic analysis of rice leaves during drought stress and recovery," *Proteomics* 2:1131-1145.
Ozawa, R. et al. (2000). "Involvement of Jasmonate- and Salicylate-Related Signaling Pathways for the Production of Specific Herbivore-Induced Volatiles in Plants," *Plant Cell Physiology* 41(4):391-398.
Yamada, S. et al. (2000). "Differential expression of plastidic aldolase genes in Nicotiana plants under salt stress," *Plant Science* 154:61-69.
Zhang, X. et al. (Feb. 2003). "Cloning of a NaCl-induced fructose-1,6-diphosphate aldolase cDNA from *Dunaliella salina* and its expression in tobacco," *Science in China (Series C)* 46(1):49-57.

* cited by examiner

*Primary Examiner* — Eileen B O'Hara
(74) *Attorney, Agent, or Firm* — Morrison & Foerster LLP

(57) ABSTRACT

Disclosed is a transgenic plant improved in growth ability and disease resistance. Also disclosed is a method for production of the transgenic plant. It is found that a transgenic plant having DNA encoding a glutathione-binding plastid-type fructose-1,6-bisphosphate aldolase introduced therein is improved in growing ability and disease resistance compared to a wild-type one.

6 Claims, 14 Drawing Sheets

(1): Col-0
(2): 049B07(T-DNA inserted mutant of FBA1)
(3): 35S-FBA1
(4): 35S-fba1C72A
(5): 35S-fba1C128A
(6): 35S-fba1C156A
(7): 35S-fba1C187A
(8): cad2-1
(9): 35S-FBA1/cad2-1

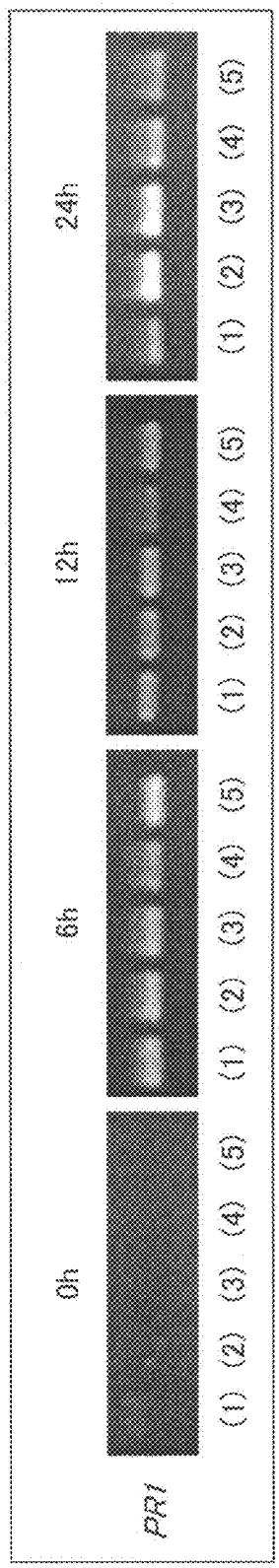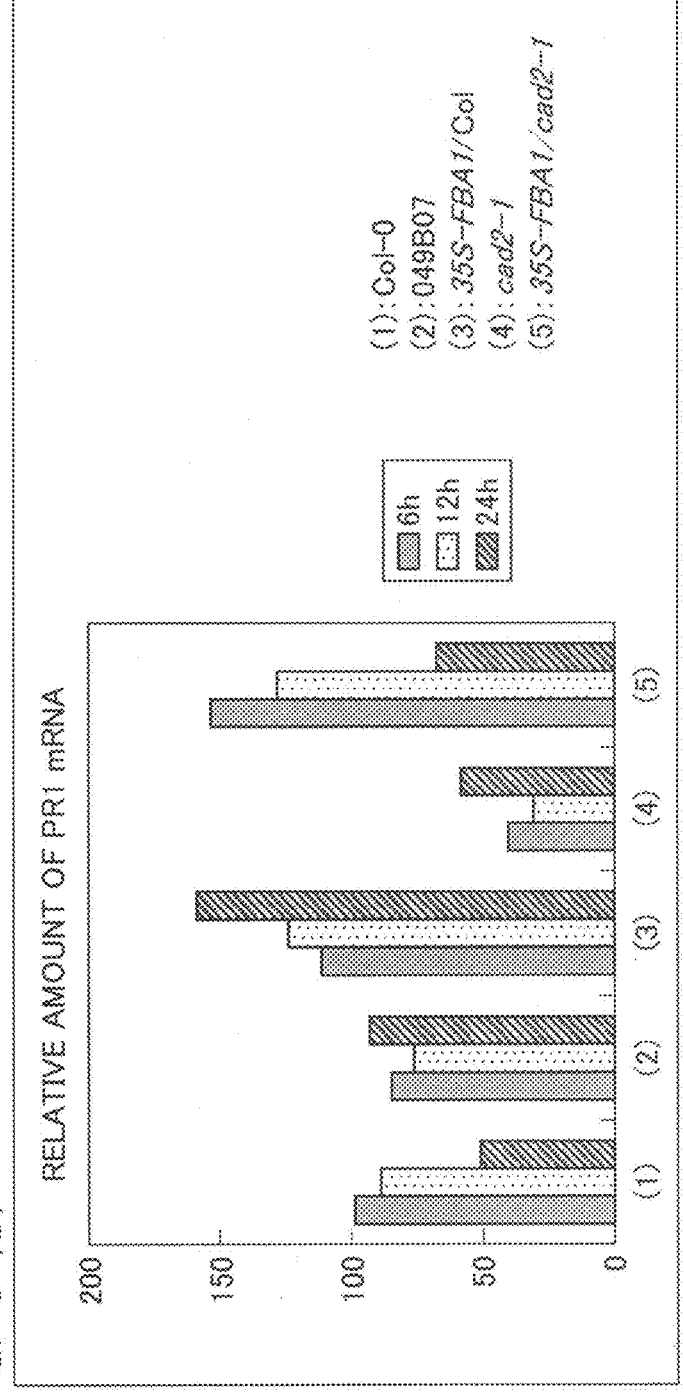
F I G. 9 (a)
F I G. 9 (b)

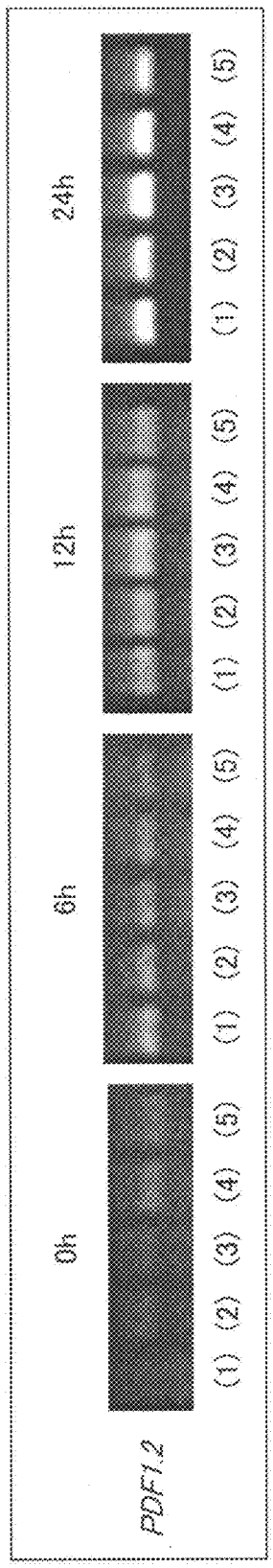
F I G. 1 0 (a)
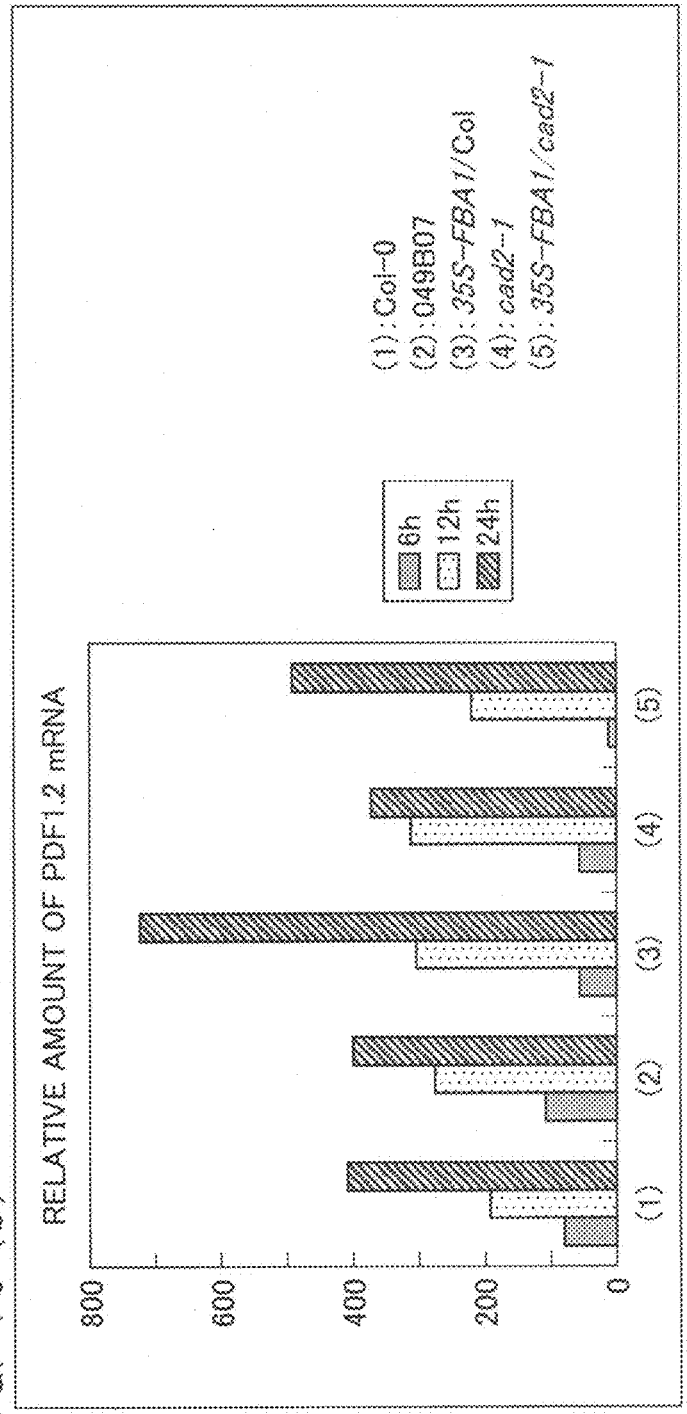
F I G. 1 0 (b)

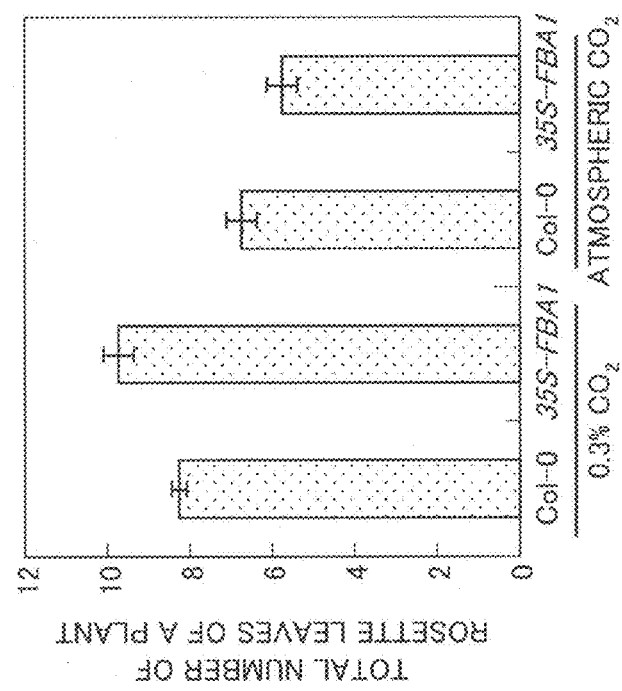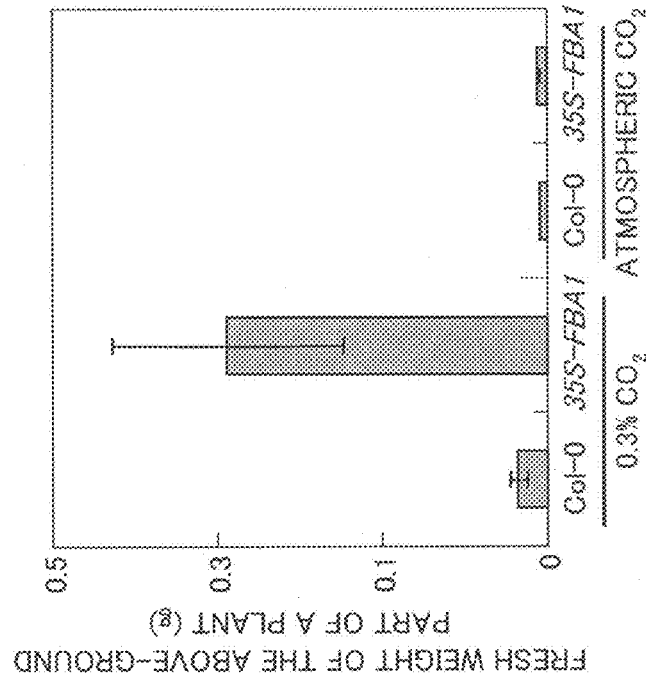
FIG. 15

PLANT HAVING IMPROVED GROWTH ABILITY AND DISEASE RESISTANCE AND METHOD FOR PRODUCTION THEREOF

CROSS REFERENCE TO RELATED APPLICATIONS

This application is a U.S. National Phase Application of PCT/JP2007/052216, filed Feb. 8, 2007, which claims priority to Japanese Patent Application No. 2006-032895 filed Feb. 9, 2006, the contents of which are both hereby incorporated by reference in the present disclosure in their entireties.

TECHNICAL FIELD

The present invention relates to a plant having improved growth ability and disease resistance for controlling the incidence caused by pests including insects and diseases, and a method for production of said plant. (Hereinafter, growth ability will be referred to as "plant growth traits", and disease resistance will be referred to as "pest controlling traits" which the translator believes are more appropriate translation of the terms.)

BACKGROUND ART

Conventionally, productivity of crops has been improved by carrying out breed improvement backed up with experience, by exterminating insects using agrichemicals, and by other methods. However, with a rapid development in molecular biology in recent years, a molecular breeding method (such as producing a transformed plant) makes it possible to develop crops having high productivity. Specific examples of techniques for improving productivity of crops encompass: promotion of growth (improvement in plant growth traits); addition of traits (i.e., pest controlling traits) for controlling the incidence caused by pests including insects and diseases; addition of stress resistance; addition of a dwarf character; control of flowering time; and the like. Beside the foregoing examples, there are various kinds of techniques leading to improvement in productivity either directly or indirectly.

The techniques directly leading to the improvement in the productivity include the promotion of plant growth (the improvement in the plant growth traits). For example, Non-Patent Document 1 reports that tobacco having overexpressed cyanobacterial fructose-1,6/sedoheptulose-1,7-bisphosphatase improves its plant growth traits. Non-Patent Document 2 discloses that *Arabidopsis thaliana* introducing Dof1 transcription factor improves its plant growth traits under low-nitrogen conditions.

Also, adding the pest controlling traits to crops improves productivity, compared with crops damaged by pests including insects and diseases. The techniques for producing a plant having the pest controlling traits by means of introducing a specific gene into a plant have been reported so far. For example, Patent Document 1 discloses such a method that transformation is carried out with a gene encoding a constitutively active form of G-protein α-subunit so as to produce rice improved in tolerance against bacterial leaf blight. Also, Patent Document 2 discloses that rice transformed with a gene encoding a defensin protein is resistive against rice blast and bacterial leaf blight.

In some cases, however, adding the pest controlling traits does not lead to improvement in productivity. For example, it is known that plant growth traits are diminished in a plant in a case where a gene related to stress resistance (including the pest controlling traits) is constitutively expressed in the plant (refer to Non-Patent Documents 3 to 5), and it is described that some kinds of efforts are necessary for the purpose of ensuring the plant growth traits.

[Patent Document 1]
Japanese Unexamined Patent Application Publication, Tokukai, No. 2005-192496 (published on Jul. 21, 2005)

[Patent Document 2]
Japanese Unexamined Patent Application Publication, Tokukai, No. 2003-88379 (published on Mar. 25, 2003)

[Non-Patent Document 1]
Miyagawa Y, Tamoi M, Shigeoka S. Overexpression of a cyanobacterial fructose-1,6-/sedoheptulose-1,7-bisphosphatase in tobacco enhances photosynthesis and growth. Nat Biotechnol. 2001 October; 19(10): 965-9.

[Non-Patent Document 2]
Yanagisawa S, Akiyama A, Kisaka H, Uchimiya H, Miwa T. Metabolic engineering with Dof1 transcription factor in plants: Improved nitrogen assimilation and growth under low-nitrogen conditions. Proc Natl Acad Sci USA. 2004 May 18; 101(20): 7833-8. Epub 2004 May 10.

[Non-Patent Document 3]
Berrocal-Lobo M, Molina A, Solano R. (2002) Constitutive expression of ETHYLENE-RESPONSE-FACTOR1 in *Arabidopsis* confers resistance to several necrotrophic fungi. Plant J. 29: 23-32.

[Non-Patent Document 4]
Kasuga M, Liu Q, Miura S, Yamaguchi-Shinozaki K, Shinozaki K. (1999) Improving plant drought, salt, and freezing tolerance by gene transfer of a single stress-inducible transcription factor. Nat Biotechnol. 17: 287-291.

[Non-Patent Document 5]
Tang X, Xie M, Kim Y J, Zhou J, Klessig D F, Martin G B. (1999) Overexpression of Pto activates defense responses and confers broad resistance. Plant Cell. 11: 15-29.

DISCLOSURE OF INVENTION

As described above, the techniques for promoting plant growth (improving the plant growth traits) and the techniques for adding the pest controlling traits to a plant have been separately researched so far. For this reason, it is required to apply two different types of techniques for the purpose of improving the plant growth traits and adding the pest controlling traits to a plant. Specifically, for example, two different genes need to be introduced to a plant for the purpose of obtaining a transformed plant in which the plant growth traits are improved and the incidence caused by pests including insects and diseases is controlled. However, there is a possibility that the transformed plant thus obtained cannot express the same phenotypes as the one obtained by introducing each of the two genes solely.

If such a technique is developed that a single technique can improve the plant growth traits and add the pest controlling traits to a plant simultaneously, the foregoing problem will not occur. Thereby, it is expected that the technique will largely contribute to improvement in productivity of crops. However, such a technique has never been reported so far.

The present invention is made in view of the foregoing problems, and has an object for providing: a transformed plant in which the plant growth traits are improved and the incidence caused by pests including insects and diseases is controlled by its traits; and a method for production of the transformed plant.

Along researching a control mechanism of active oxygen in plant growth, the inventors of the present invention identified glutathione-binding plastid-type fructose-1,6-bisphosphate aldolases in cultured cells of *Arabidopsis thaliana* and isolated chloroplasts of *Arabidopsis thaliana* and *Spinacia oleracea*. A gene encoding the protein was cloned from wild-type *Arabidopsis thaliana*, a recombinant protein was expressed in *Escherichia coli* from the cloned gene, and the protein was analyzed for its function. In the researching process, *Arabidopsis thaliana* was transformed with the glutathione-binding plastid-type fructose-1,6-bisphosphate aldolase, and then it was found that the transformed plant had improved plant growth traits compared with the wild-type plant. Further, it was found that the incidence caused by pests including insects and diseases was also controlled in the transformed plant. The present invention was accomplished on these findings.

That is, a transformed plant related to the present invention is a transformed plant wherein: a DNA encoding a glutathione-binding plastid-type fructose-1,6-bisphosphate aldolase is introduced; as a consequence, plant growth traits are improved and the incidence caused by pests including insects and diseases is controlled.

A method for producing a plant according to the present invention in which plant growth traits are improved and the incidence caused by pests including insects and diseases is controlled includes the step of: introducing, to a plant, a DNA encoding a glutathione-binding plastid-type fructose-1,6-bisphosphate aldolase.

In a transformed plant according to the present invention and in a method for producing the plant according to the present invention in which plant growth traits are improved and the incidence caused by pests including insects and diseases is controlled, it is preferable that a DNA encoding a glutathione-binding plastid-type fructose-1,6-bisphosphate aldolase is selected from the group consisting of the following (a) through (d):

(a) a DNA encoding a protein having the amino acid sequence shown in SEQ ID NO: 1;

(b) a DNA encoding a protein having an amino acid sequence with deletion, substitution, or addition of one or several amino acids in the amino acid sequence shown in SEQ ID NO: 1;

(c) a DNA having the base sequence shown in SEQ ID NO: 2; and (d) a DNA that hybridizes under stringent conditions with a DNA having the base sequence shown in SEQ ID NO: 2.

The present invention makes it possible to produce, by introducing a single gene into a plant, a plant in which plant growth traits are improved and the incidence caused by pests including insects and diseases is controlled. Therefore, the present invention can largely contribute to improvement in productivity of crops and in biomass productivity. Also, the present invention can significantly reduce the amount of chemical fertilizer and agrichemicals to be used.

Further, if the present invention is applied to a plant which is suitable as raw materials, it is expected that the plant produced by the present invention can be used as an alternative to various kinds of industrial raw materials or energy source, although now we are mostly dependent on crude oil for the industrial raw materials or the energy source because of its cost.

Additional objects, features, and strengths of the present invention will be made clear by the description below. Further, the advantages of the present invention will be evident from the following explanation in reference to the drawings.

BRIEF DESCRIPTION OF DRAWINGS

FIG. 9 (*a*) shows electrophoretograms illustrating the result of electrophoresis carried out for products of RT-PCR of PR1 mRNA obtained from five types of *Arabidopsis thaliana* (Col-0, 35S-FBA1/Col-0, cad2-1, 35S-FBA1/cad2-1, and 049B07) subjected to salicylate treatment.

FIG. 9 (*b*) is a graph illustrating the relative amount of PR1 mRNA obtained from five types of *Arabidopsis thaliana* (Col-0, 35S-FBA1/Col-0, cad2-1, 35S-FBA1/cad2-1, and 049B07) subjected to salicylate treatment.

FIG. 10 (*a*) shows electrophoretograms illustrating the result of electrophoresis carried out for products of RT-PCR of PDF1.2 mRNA obtained from five types of *Arabidopsis thaliana* (Col-0, 35S-FBA1/Col-0, cad2-1, 35S-FBA1/cad2-1, and 049B07) subjected to jasmonate treatment.

FIG. 10 (*b*) is a graph illustrating the relative amount of PDF1.2 mRNA obtained from five types of *Arabidopsis thaliana* (Col-0, 35S-FBA1/Col-0, cad2-1, 35S-FBA1/cad2-1, and 049B07) subjected to jasmonate treatment.

FIG. 15 shows graphs comparing, in (i) fresh weight of the above-ground part of a plant and in (ii) the total number of rosette leaves of a plant, between: wild-type *Arabidopsis thaliana* (Col-1); and transformed *Arabidopsis thaliana* (35S-FBA1) into which an FBA1 gene was introduced, each of which was grown up (a) under the same CO2 condition as in the atmosphere and (b) under a high CO2 condition.

BEST MODE FOR CARRYING OUT THE INVENTION

Figure 1:
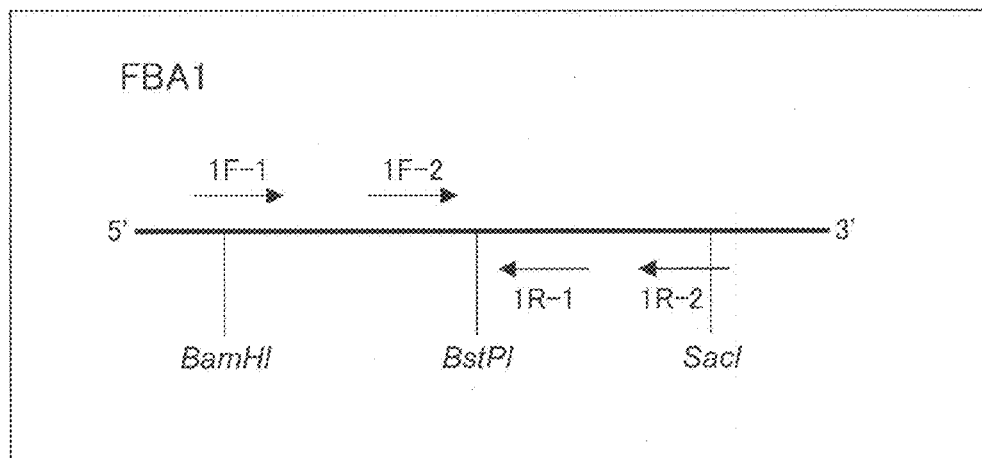
FIG. 1 is a view illustrating primers and restriction enzyme sites used for cloning of an FBA1 gene.

Firstly, the following briefly describes the background of the processes through which the present invention was accomplished.

The inventors of the present invention demonstrated (i) that active oxygen of appropriate concentration was necessary for a plant not only as a substrate in biosynthesis, but also as a control factor in plant growth; and (ii) that plant growth can be improved by treating a seed, a plant body, a leaf, or a root with active oxygen of appropriate concentration. Also, the inventors showed that a growth enhancement effect of the active oxygen was associated with glutathione in a cell. Through the research, the inventors screened glutathione-binding proteins in cultured cells of *Arabidopsis thaliana*, thereby identifying a protein which was deduced to be a plastid-type fructose-1, 6-bisphosphate aldolase (Ito, H., Iwabuchi, M. and Ogawa, K. (2003) Plant Cell Physiol. 44, 655-660).

After that, the inventors cloned a cDNA encoding the protein from wild-type *Arabidopsis thaliana*, expressed a recombinant protein in *Escherichia coli* from the cloned gene, and purified the recombinant protein so as to analyze its function.

It is predicted that *Arabidopsis thaliana* has at least seven genes deduced to encode a fructose-1,6-bisphosphate aldolase (hereinafter, referred to as "FBA") and that three genes out of the seven genes are targeted to a plastid. Out of the three FBAs, the inventors named the glutathione-binding FBA as "FBA1" and the other two FBAs as "FBA2" and "FBA3", respectively. Then, FBA1 through FBA3 were subjected to an experiment. As a result, the following facts were revealed:

1) a recombinant FBA1 has an FBA activity;
2) the recombinant FBA1 is controlled by glutathione; and
3) all of FBA1, FBA2, and FBA3 are suppressed by dithiothreitol or reduced-thioredoxin (Trx), but only FBA1 is activated again by the glutathione.

In addition, it was indicated that FBA1 is present in chloroplast actually because the FBA activity was lost in chloroplast isolated from a T-DNA inserted mutant of an FBA1 gene ("Ogawa, K., Matsumoto, M. and Ito, H., (2005) Vol. 1, Photosynthesis: Fundamental Aspects to Global Perspectives, edited by Van der Est A and Bruce D. Lawrence, Allen Press, Inc., 468-469", "Matsumoto, M. and Ogawa, K., Abstracts of the 23rd Japanese society for plant cell and molecular biology symposium (Dai 23 kai nihon shokubutsu saibou bunshi seibutsu gakkai taikai simpojiumu youshi shu), issued on Aug. 4, 2005").

In order to further proceed with the research, the inventors introduced an FBA1 gene into wild-type *Arabidopsis thaliana*, and thereby produced a transformed plant. As a result, it was found that plant growth traits were improved and the incidence caused by pests including insects and diseases was controlled in the *Arabidopsis thaliana* transformed with FBA1.

The following describes in detail a transformed plant according to the present invention and a method of production thereof.

The present invention provides: a transformed plant wherein a DNA encoding a glutathione-binding plastid-type fructose-1,6-bisphosphate aldolase (FBA1) is introduced, and as a consequence, plant growth traits are improved and the incidence caused by pests including insects and diseases is controlled; and a production method thereof.

In the present invention, the phrase "plant growth traits are improved" means that a plant to which a DNA encoding FBA1 is introduced has a larger extent of growth or has a faster growing speed, compared with a plant to which the DNA encoding FBA1 is not introduced. More specifically, the phrase "plant growth traits are improved" means that the plant to which the DNA encoding FBA1 is introduced has a heavier raw weight or dry weight, has a seed or a fruit in a larger production amount or of a heavier dry weight, or has a larger number of leaves, compared with the plant to which the DNA encoding FBA1 is not introduced.

Also, in the present invention, the phrase "the incidence caused by pests including insects and diseases is controlled" means that the plant to which the DNA encoding FBA1 is introduced has the following features more outstandingly, compared with the plant to which the DNA encoding FBA1 is not introduced: (i) the progress of a disease caused by pathogenic fungi or bacteria can be delayed or the disease can be alleviated; (ii) the progress of verminous damages caused by an insect can be delayed or the verminous damage can be reduced. The control of the incidence caused by insects herein refers to: (i) a repellent effect achieved by production of a repellent substance against the insect; and (ii) extermination effect or a growth preventive effect for the insect achieved by production of a substance for attracting its natural enemy or production of a toxic substance against the insect.

The glutathione-binding plastid-type fructose-1,6-bisphosphate aldolase (hereinafter, referred to as "FBA1") encoded in the DNA to be used in the present invention only needs to have an FBA activity, to exist in a plastid such as chloroplast, and to control its activity by glutathione. Also, the kind of the plant from which the DNA is derived is not particularly limited. It has been suggested that FBA1 exists in many kinds of plants. This is supported by the following facts: (i) it is known that an FBA activity in chloroplast conventionally measured by using a biochemical method exhibits pH dependence as well as FBA1 of *Arabidopsis thaliana* does; and (ii) it is easily expected that optimum pH for an enzyme functioning inside stroma of chloroplast during photosynthesis is around 8, at which photosynthesis takes place. The FBA activity refers to activity for reversibly catalyzing a reaction in which a fructose-1,6-bisphosphate is converted into a dihydroxyacetone phosphate and a glyceraldehydes-3-phosphate.

The DNA encoding FBA1 used in the present invention may be an FBA1 gene derived from *Arabidopsis thaliana*. The FBA1 derived from *Arabidopsis thaliana* has the amino acid sequence shown in SEQ ID NO: 1, and a gene (full-length cDNA) encoding FBA1 has the base sequence shown in SEQ ID NO: 3. Of the base sequence shown in SEQ ID NO: 3, position 145 to position 147 are an initiation codon; and position 1318 to position 1320 are a stop codon. That is, the

*Arabidopsis thaliana* FBA1 gene has an open reading frame (ORF) consisting of the region between position 145 and position 1320 of the base sequence shown in SEQ ID NO: 3. The base sequence shown in SEQ ID NO: 2 is the base sequence of the ORF of the *Arabidopsis thaliana* FBA1 gene. Genes being homological with the base sequence of the *Arabidopsis thaliana* FBA1 gene encompass a gene (dbj|BAB55475.1) present on a genome of rice.

In the present invention, it is preferable to use a DNA encoding a protein having an amino acid sequence with deletion, substitution, or addition of one or several amino acids in the amino acid sequence shown in SEQ ID NO: 1, and having an FBA1 activity. As shown in the Example described later, the inventors exemplified that the plant growth traits were improved, as well as in *Arabidopsis thaliana* into which a DNA encoding FBA1 having no mutation was introduced, in *Arabidopsis thaliana* into which either of the following types of DNA was introduced: (i) a DNA encoding FBA1 mutated so as to substitute cysteine of position 72 in the amino acid sequence of *Arabidopsis thaliana* FBA1 (SEQ ID NO: 1) with another amino acid (alanine, in the Example); (ii) a DNA encoding FBA1 so as to substitute cysteine of position 187 in the amino acid sequence of *Arabidopsis thaliana* FBA1 (SEQ ID NO: 1) with another amino acid (alanine, in the Example).

The phrase "deletion, substitution, or addition of one or several amino acids" herein means that a certain number (preferably 10 or less, more preferably 7 or less, further more preferably 5 or less) of amino acids are deleted, substituted, or added. The certain number of amino acids should be within the range in which the amino acids can be deleted, substituted, or added by using a well-known mutated peptide producing method such as site-directed mutagenesis techniques. Such a mutated protein is not limited to a protein having a mutation artificially introduced by a well-known mutated polypeptide producing method, but may be a protein obtained by isolation and purification of a naturally-occurring protein.

It is well-known in this field that some amino acids can be altered in an amino acid sequence of a protein without being significantly affected in the structure or function of the protein. Also, it is well-known that, in addition to the artificial mutant, a naturally occurring mutant exists in which the structure or function is not significantly altered from that of its natural protein because of its mutation.

A preferable mutant has conservative or non-conservative substitution, deletion, or addition of an amino acid. Silent substitution, addition, or deletion is preferable. Especially, the conservative substitution is preferable. These do not alter an activity of the polypeptide related to the present invention.

The typical conservative substitution includes: the substitution, one for another, among the aliphatic amino acids Ala, Val, Leu, and Ile; interchange of the hydroxyl residues Ser and Thr; interchange of the acidic residues Asp and Glu; substitution between the amide residues Asn and Gln; interchange of the base residues Lys and Arg; and substitution between the aromatic residues Phe and Tyr.

In the present invention, a DNA (a first DNA) may be used which hybridizes under stringent conditions with a DNA (a second DNA) having the base sequence shown in SEQ ID NO: 2, provided that the first DNA encodes a protein having an FBA1 activity. The first DNA may be, for example, a DNA encoding a protein having an amino acid sequence with deletion, substitution, or addition of one or several amino acids in the amino acid sequence shown in SEQ ID NO: 1.

The "stringent conditions" in the present invention means that hybridization occurs only when at least 90% identity, preferably at least 95% identity, or most preferably at least 97% identity exists between sequences. Specifically, the following condition is an example of the stringent conditions: (i) a hybridization filter is incubated overnight at 42° C. in hybridization solution (including 50% formamide, 5×SSC (150 mM NaCl, 15 mM trisodium citrate), 50 mM sodium phosphate (pH 7.6), 5×Denhardt's solution, 10% dextran sulfate, and 20 mg/ml of denatured, sheared salmon sperm DNA); and then (ii) the filter is washed in 0.1×SSC at approximately 65° C.

The hybridization may be carried out by using a well-known method as described in "Sambrook et al., Molecular Cloning, A Laboratory Manual, 3rd Ed., Cold Spring Harbor Laboratory (2001)". Normally, an increased temperature and lowered salt concentration enhance stringency (i.e., make it difficult to hybridize), thereby allowing to obtain a DNA having higher homology.

The identity in an amino acid sequence or a base sequence may be determined by using an algorism BLAST by Karlin and Altschul (Karlin S, Altschul S F, Proc. Natl. Acad. Sci. USA, 87: 2264-2268 (1990); Karlin S, Altschul S F, Proc. Natl. Acad. Sci. USA, 90: 5873-5877 (1993)). Based on the algorism BLAST, programs called BLASTN or BLASTX have been developed (Altschul S F, et al., J. Mol. Biol., 215: 403 (1990)).

The DNA encoding FBA1 used in the present invention may be derived either from a genomic DNA or a cDNA, or may be a chemically-synthesized DNA.

The DNA encoding FBA1 used in the present invention can be obtained by isolating and cloning DNA fragments encoding FBA1 using known techniques. For example, a probe is prepared that specifically hybridizes with a portion of a DNA encoding *Arabidopsis thaliana* FBA1, and a genomic DNA library or a cDNA library is screened with the probe.

Alternatively, the DNA encoding FBA1 used in the present invention can be obtained by amplification means such as PCR. For example, primers for PCR are prepared based on the 5' and 3' ends of the sequence (or its complementary sequence) of the cDNA encoding the *Arabidopsis thaliana* FBA1; and, by using the primers, PCR or other means is conducted with a genomic DNA (or a cDNA) as a template so as to amplify the DNA region between the primers. In this way, DNA fragments encoding FBA1 used in the present invention can be obtained in mass quantity.

The DNA used in the present invention can be obtained from a tissue or a cell of an appropriate plant as a source. The kind of the plant may be, but are not limited to, for example, other cruciferous plants which are closely related to *Arabidopsis thaliana*, such as rice, tobacco, oil palm, poplar, and the like. As described above, it is suggested that many kinds of plants have a protein having an FBA1 activity, and therefore, a person skilled in the art can easily expect that plants other than *Arabidopsis thaliana* also have a DNA encoding FBA1.

In the present invention, as a method for introducing a DNA encoding FBA1 into a plant, such a method is preferably used that a recombinant expression vector is constructed so as to have a promoter functioning in a plant cell connected to the upstream of a DNA encoding FBA1 and a terminator functioning in a plant cell connected to the downstream of the DNA, and is introduced into a plant.

In the embodiment described later, the promoter functioning in a plant cell may be, but are not limited to a cauliflower mosaic virus 35S promoter which is constitutively expressed. A promoter capable of being expressed constitutively other than the cauliflower mosaic virus 35S promoter may be an actin promoter of rice, a ubiquitin promoter of corn, or the like. These promoters may be preferably used in the present invention as well.

A promoter capable of being expressed constitutively other than the foregoing promoters may be, but are not limited to: a green leaf tissue-specific promoter such as an rbcS promoter and a Cab promoter; and an inducible promoter such as an HSP70 promoter. A promoter to be directly inserted into a genome of chloroplast may be, but are not limited to an rbcL promoter or the like, and may be any promoter which can function in chloroplast.

The terminator functioning in a plant cell may be a terminator derived from a nopaline synthetic enzyme (NOS) gene, a terminator derived from a cauliflower mosaic virus, or the like.

A recombinant expression vector used for transformation of a plant is not particularly limited to a specific kind, as far as a gene inserted in the recombinant expression vector can be expressed in a plant cell. It is preferable to use binary vectors (such as of pBI system) when Agrobacterium is used for introducing a vector into a plant. Examples of the binary vectors may include pBIG, pBIN19, pBI101, pBI121, pBI221, and the like.

The plants to be transformed in the present invention may be any of the followings: whole plants; plant organs (such as a leaf, a petal, a stem, a root, a seed, and the like); plant tissues (such as epidermis, phloem, parenchyma, xylem, a fibrovascular bundle, a palisade tissue, a cancellous tissue, and the like); plant culture cells; and various forms of plant cells (such as suspended culture cells); protoplasts; leaf slices; calluses, and the like. The kind of the plant used for transformation is not particularly limited, and it may be a plant capable of expressing the DNA encoding FBA1 which is used.

When the DNA encoding the Arabidopsis thaliana FBA1 is used, cruciferous plants, which are closely related to Arabidopsis thaliana, are preferable for the plants to be transformed. However, the plant used in the present invention is not limited to these. It is reported that a transformed plant can be produced from the plants such as tobacco, poplar, and citrus by using an Arabidopsis thaliana gene (Franke R, McMichael C M, Meyer K, Shirley A M, Cusumano J C, Chapple C. (2000) Modified lignin in tobacco and poplar plants over-expressing the Arabidopsis gene encoding ferulate 5-hydroxylase. Plant J. 22: 223-234; Pena L, Martin-Trillo M, Juarez J, Pina J A, Navarro L, Martinez-Zapater J M. (2001) Constitutive expression of Arabidopsis LEAFY or APETALA1 genes in citrus reduces their generation time. Nat Biotechnol. 19: 263-267). Therefore, it is considered that various kinds of transformed plants in which plant growth traits are improved and the incidence caused by pests including insects and diseases is controlled can be produced by introducing the DNA encoding the Arabidopsis thaliana FBA1 into the foregoing plants.

A recombinant expression vector may be introduced into a plant cell by a transformation method known in the art, for example, an Agrobacterium method, a particle gun method, a polyethyleneglycol method, an electroporation method, and the like. For example, when the Agrobacterium method is used, a transformed plant can be obtained by (i) introducing an expression vector constructed for plants into a suitable Agrobacterium (such as Agrobacterium tumefaciens), and (ii) infecting, with the resulting strains, leaflets cultured under an aseptic condition, in accordance with techniques such as a leaf disc method (Uchimiya, H., Plant gene manipulation manual (Shokubutsu idenshi sousa manyuaru), 1990, pp. 27-31, Kodansha Scientific, Tokyo, Japan).

When the particle gun method is used, it is possible to use a plant, a plant organ, or a plant tissue either directly or in the form of a slice or a protoplast which is prepared. The samples thus prepared may be processed by using a gene introducing device (such as PDS-1000 of BIO-RAD). Generally, the particle gun method is conducted under the pressure of approximately 450 psi to 2000 psi, and at the distance of approximately 4 cm to 12 cm, and such conditions can vary depending on the type of a plant or a sample.

The cells or the plant tissues into which a DNA of interest is introduced are first selected based on a drug resistance marker such as kanamycin resistance or hygromycin resistance and then are regenerated into plants by using ordinary methods. The regeneration of plants from transformed cells may be carried out by using methods known in the art in accordance with the type of plant cells.

Whether or not the DNA of interest was successfully introduced into a plant may be determined, for example, by using a PCR method, a southern hybridization method, a northern hybridization method, or the like. For example, whether or not the transformation has been successfully carried out can be confirmed according to the following steps: preparing a DNA library from a transformed plant; designing primers specific to the DNA of interest; conducting PCR with the DNA library and the primers; subjecting amplified products to agarose gel electrophoresis, polyacrylamide gel electrophoresis, capillary electrophoresis or the like; staining with ethidium bromide or the like; and detecting an amplified product of interest.

Once a transformed plant is obtained in which a DNA encoding FBA1 is introduced into a genome, offspring of the plant can be obtained by reproducing the plant either sexually or asexually. Further, it is possible to produce the desired plant in mass quantity from materials for reproduction (such as a seed, a protoplast, and the like), the materials being obtained from the plant, its offspring, or its clone.

The transformed plant thus obtained in the foregoing manner is expected to have more improved plant growth traits and pest controlling traits, compared with a wild-type plant. It is possible to confirm whether or not the plant growth traits is improved by comparing, in sizes, weights, and the like, between a transformed plant and a wild-type plant each of which is seeded at the same time. Also, it is possible to confirm whether or not the incidence caused by pests including insects and diseases can be further controlled, by comparing between a transformed plant and a wild-type plant in disease states after they are inoculated with, for example, Colletotrichum higginsianum (as in the Example described later).

The plant growth traits of a transformed plant according to the present invention are improved as follows. In transformed Arabidopsis thaliana, the plant growth traits are enhanced by 10% to 15% or more even under extremely low light intensity (approximately 1/50 of sun light). Further, it is expected that the plant growth traits are enhanced by approximately 30% to 40% or more when the light intensity is doubled, and are enhanced by approximately 70% to 80% or more when the light intensity is increased to approximately 3/20 of sun light. When $CO_2$ concentration is increased, the transformed plant exhibits twice to three times or more as much plant growth traits as a normal plant exhibits. Further, under preferable conditions, the transformed plant exhibits 10 times to 20 times or more as much plant growth traits as a normal plant exhibits in increased $CO_2$ concentration. The plants thus produced can grow up even in a place having limited light intensity (such as in a forest floor). This increases an area where plants can grow up. In addition, the plant growth traits are largely improved under high luminosity. Therefore, it is expected that productivity of crops is significantly enhanced in an open area such as a cultivated field. Further, it is expected that applying the present invention to plants which draw attention as industrial material or energy source material can significantly reduce a production cost of the plants, so as to make the plants become an alternative to oil. Also, it is expected that applying the present invention to trees for pulp (such as poplar) can attain effective forestation and nurturing of a forest, so as to restrain possible deforestation in the future. It is expected that applying the present invention to plants in an arid region can improve productivity of the plants in the arid region, so as to contribute to acceleration of greening or prevention of desertification.

In view of the control of the incidence caused by pests including insects and diseases, a transformed plant according to the present invention possesses a wide spectrum over not only fungi but also pests including bacteria and insects. Salicylate and jasmonate, each of which is produced when a plant is infected with pathogenic bacteria, are signal substances important for controlling the incidence caused by pests including insects and diseases. A transformed plant according to the present invention has an outstanding feature such that it is improved in both of the salicylate and the jasmonate responses for controlling the incidence caused by pests including insects and diseases. This feature cannot be found in conventional plants. Also, the jasmonate is known as a substance related to the traits for controlling the incidence caused by insects ("Ozawa, R., Arimura, G., Takabayashi, J., Shimoda, T., and Nishioka, T. (2000) Involvement of jasmonate- and salicylate-related signaling pathways for the production of specific herbivore-induced volatiles in plants, Plant Cell Physiol. 41, 391-398.", "Takabayashi, J. ed. (2003) Protein, nucleic acid and enzyme (Tampakushitsu, kakusan, kouso), vol. 48 (13), October, 2003"). Therefore, a person skilled in the art can easily understand that a transformed plant according to the present invention can further control the incidence caused by insects.

EXAMPLES

The present invention will be described in detail in Examples. It should be noted that the present invention is not limited to the Examples.

(1) A Plant to be Used

For wild-type *Arabidopsis thaliana*, Columbia (Col-0) was used. A mutant cad2-1 in which the amount of endogenous glutathione was reduced (Howden, R., Anderson, C. R., Goldsbrough, P. B. and Cobbett, C. S. (1995) A cadmium-sensitive, glutathione-deficient mutant of *Arabidopsis thaliana*. Plant Physiol. 107: 1067-1073) was provided by Dr. Christopher S. Cobbett (The University of Melbourne, Parkville, Australia).

The plants were seeded in a square plastic pot (6.5×6.5×5 cm) filled with three-layer soil having layers of vermiculite (Asahi-Kogyo, Okayama, Japan), Kureha culture soil (Kureha garden cultivating soil, Kureha Co., Tokyo, Japan), and vermiculite, from the bottom. The layers were made in a ratio of 2:2:1 (in the order listed above). Then, plants were grown up under a long day condition (16 h light/8 h dark) at 22° C. of a growth temperature, or under a short day condition (10 h light/14 h dark) at 22° C. of a growth temperature.

(2) Cloning an FBA1 Gene, Producing a Mutated FBA1 Gene, and Producing an FBA1-Overexpressed Transformed Plant Total RNA was isolated from the wild-type *Arabidopsis thaliana* Columbia (Col-0) at the age of 4 weeks. Then, RT-PCR (the amount of template RNA: 5.0 μg) was carried out by using Prostar first strand RT-PCR kit (Stratagene, La Jolla, Calif., U.S.A.), so that a cDNA was produced.

As illustrated in FIG. 1, the following specific primers which were designed based on a cDNA sequence (SEQ ID NO: 3) of FBA1 were used so that two fragments of full-length cDNA were amplified by PCR. Then, each of the fragments was TA-cloned to a pGEM-T vector (Promega, Madison, Wis., U.S.A.).

```
                                            (SEQ ID NO: 4)
1F-1:  5'-GGATCCTATGGCGTCTGCTAG-3'

(SEQ ID NO: 5)
1R-1:  5'-ATCTGCAACGGTCTCGGGAGA-3'

(SEQ ID NO: 6)
1F-2:  5'-GTGTGGTCCGAGGTGTTCTTCT-3'

(SEQ ID NO: 7)
1R-2:  5'-GAGCTCGAGTAGGTGTAACCCTTG-3'
```

The two fragments were fused at a BstpI site, so that a vector (pGEM-FBA1) including full-length cDNA was constructed. For the purpose of producing a transformed plant, the pGEM-FBA1 was processed by restriction enzymes BamHI and SacI, and then the fragments were introduced into a pBI121 vector.

Further, four constructs for expressing mutated FBA1 proteins (fba1C72A, fba1C128A, fba1C156A, and fba1C187A, respectively) were produced. In the four constructs, different one of four cysteine residues in an FBA1 protein was substituted with an alanine residue respectively. All of the four cysteine residues were encoded in a construct including a BamHI-BstpI fragment out of the two fragments of cDNA which were used for producing the pGEM-FBA1. In view of this, PCR was first carried out by using a combination of a primer pGEM-del-ApaI and a primer SP6, so as to amplify a fragment in which a multiple-cloning site was deleted from the pGEM vector. Then, PCR was first carried out by using a combination of a primer T7 and any one of primers Ald-C72A, Ald-C128A, Ald-C156A, or Ald-C187A, so as to obtain a fragment in which site-directed mutagenesis was introduced. The foregoing PCR was carried out in one cycle of 95° C. for 5 minutes and in 30 cycles of 94° C. for 30 seconds, 60° C. for one minute, and 72° C. for one minute.

```
                                            (SEQ ID NO: 8)
T7:    5'-CCGCTGAGCAATAACTAGC-3'

(SEQ ID NO: 9)
SP6:   5'-ATTTAGGTGACACTATAGAAT-3'

(SEQ ID NO: 10)
pGEM-del-ApaI:  5'-TCACTATAGGGCGAATTGGTACCGA-3'

(SEQ ID NO: 11)
Ald-C72A:   5'-AATGCAACCGCTGGGAAGAGG-3'

(SEQ ID NO: 12)
Ald-C128A:  5'-TTTGTCGATGCCTTGCGCGATG-3'

(SEQ ID NO: 13)
Ald-C156A:  5'-GTCTTGGGCCCAAGGCTTGG-3'

(SEQ ID NO: 14)
Ald-C187A:  5'-AGTGTTCCCGCCGGTCCTTCA-3'
```

Then, 0.5 μl each of two PCR products thus obtained was mixed, thermally denatured, and slowly cooled down (94° C. for 10 minutes, 37° C. for 15 minutes, and 4° C. for 35 minutes). After 0.5 μl of LA-Taq (TAKARA BIO Inc., Tokyo, Japan) was added therein, heat treatment thereof was carried out at 72° C. for 3 minutes. Further, the primer T7 (10 μM) and the primer SP6 (10 μM) were added therein, and PCR thereof was carried out in 10 cycles of 94° C. for 30 seconds, 57° C. for one minute, and 72° C. for one minute. Then, PCR fragments thus obtained were digested by using restriction enzymes ApaI and BamHI, and sub-cloned to a pBluscript SK vector. After the subcloning process, the digestion fragments of BamHI and BstpI were fused with another cDNA fragment (the BstpI-SacI fragment), so as to be introduced to a pBI121 expression vector.

The pBI121 expression vectors thus prepared in accordance with the foregoing procedure were introduced to Col-0 and cad2-1 by using the *Agrobacterium* method (Clough, S. J. and Bent, A. F. (1998) Floral dip: A simplified method for *Agrobacterium*-mediated transformation of *Arabidopsis thaliana*. Plant J. 16: 735-743), so that a transformed plant was produced.

Specifically, a selection process was repeatedly carried out on an agar medium (½ concentration of a Murashige-Skoog medium) containing kanamycin, which was a selection marker. After such a phase that all seeds could grow up on the medium containing the kanamycin (i.e., a generation in which the characters were not segregated) was attained, the expression level of the introduced gene was measured by using RT-PCR analysis, and thereby the production of a transformed plant was confirmed. Before the RT-PCR was carried out, RNA was extracted from three matured leaves of transformed *Arabidopsis thaliana* at the age of 4 weeks by using RNeasy Plant Mini Kit (QIAGEN, Valencia, Calif., U.S.A.), and a cDNA was prepared by using Prostar first Strand RT-PCR Kit (Stratagene, La, jolla, Calif., U.S.A.). Then, the RT-PCR was carried out in 26 cycles (94° C. for 30 seconds, 58° C. for 60 seconds, and 72° C. for 60 seconds), by using reaction solution including 7.5 µl of premix EX-taq (TaKaRa, Otsu, Shiga, Japan); 2 µl of FBA1-F primer (1.33 µM); 2 µl of FBA1-R primer (1.33 µM); 2 µl of cDNA template (0.025 µg); and 1.5 µl of H2O. A Tubulin gene, whose expression was confirmed constitutively, was used as a control. The RT-PCR for Tubulin was carried out in 22 cycles (94° C. for 30 seconds, 58° C. for 60 seconds, and 72° C. for 60 seconds), by using: a primer set of Tublin-F and Tublin-R; and the same reaction solution used in the foregoing RT-PCR. The PCR product was confirmed by 1.2% agarose gel electrophoresis, and measured quantitatively by using Agilent Technologies 2100 Bioanalyzer (Agilent Technologies, Hachioji, Japan).

```
                                              (SEQ ID NO: 15)
FBA1-F:  5'-TCTGCTAGCTTGGTTAAGCCTAAC-3'

(SEQ ID NO: 16)
FBA1-R:  5'-GGCATCGCGCAAGCAATCGACAAA-3'

(SEQ ID NO: 17)
Tubulin-F:  5'-GTCCAGTGTCTGTGATATTGCAC-3'

(SEQ ID NO: 18)
Tubulin-R:  5'-GCTTACGAATCCGAGGGTGC-3'
```

Figure 2:
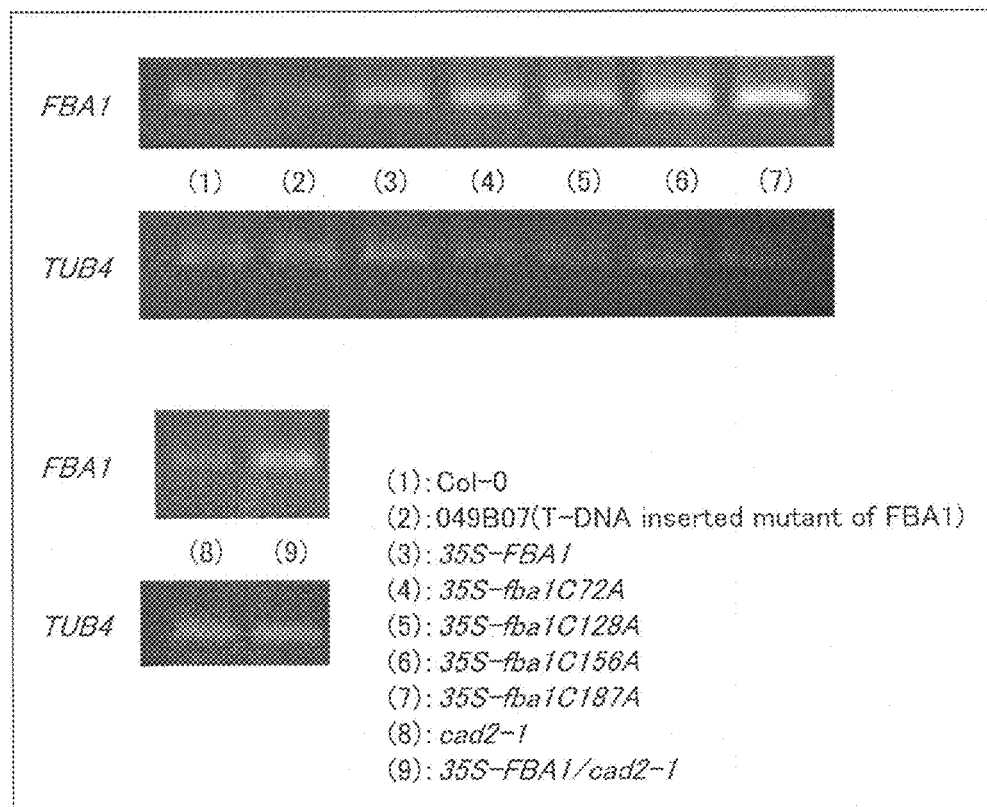
FIG. 2 shows electrophoretograms illustrating the result of electrophoresis carried out for products of RT-PCR of FBA1 mRNA obtained from a transformed plant into which an FBA1 gene was introduced.

FIG. 2 shows the result of the electrophoresis. Tubulin was a control gene whose expression could be confirmed constitutively under the growth conditions in the present Examples. As is clear from FIG. 2, it was confirmed that 35S-FBA1, 35S-fba1C72A, 35S-fba1C128A, 35S-fba1C156A, and 35S-fba1C187A had an increased amount of FBA1 mRNA, compared with the wild type (Col-0). Similarly, it was confirmed that 35S-FBA1/cad2-1 had an increased amount of FBA1 mRNA, compared with cad2-1.

In the present Example, an expression vector was constructed by using a cDNA. Other than this, a person skilled in the art can easily understand that a transformed plant can be obtained by (i) cloning an FBA1 gene including intron from a genomic DNA, (ii) constructing an expression vector with the gene, and (iii) introducing the expression vector into a plant.

(3) A T-DNA Inserted Mutant of an FBA1 Gene

Figure 3:
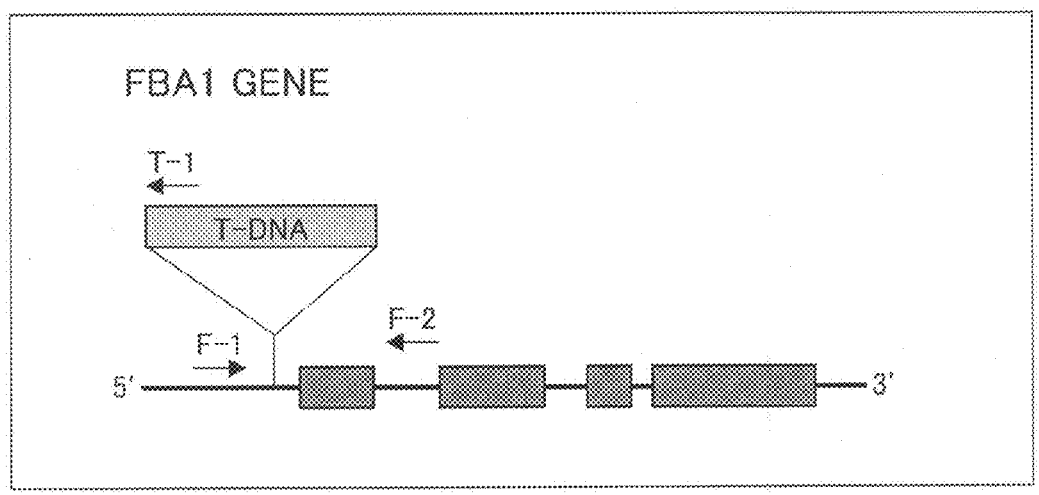
FIG. 3 is a view illustrating a position at which T-DNA was inserted in a T-DNA inserted mutant (049B07) of an FBA1 gene.

From GABI-Kat (Germany, www.gabi-kat.de/db), seeds (in a heterogenous state) of a mutant (GK Line ID 049B07) in which T-DNA was inserted into an *Arabidopsis thaliana* FBA1 gene were commercially provided. FIG. 3 shows a position at which T-DNA is inserted. As illustrated in FIG. 3, the following primers specific to the T-DNA and the FBA1 gene were designed, and homogenous mutants were selected by PCR using a genomic DNA as a template.

```
                                              (SEQ ID NO: 19)
T-1:  5'-CTGGTTTGCCCCAGCAGGCGAAA-3'

(SEQ ID NO: 20)
F-1:  5'-GGGGAATAAAATGGTAAAGAGAAGGAGGC-3'

(SEQ ID NO: 21)
F-2:  5'-GCAATAATCAGAGAATCTCACTCT-3'
```

Specifically, the following procedures were carried out.

The seeds provided by GABI-Kat were seeded, and two leaves were cut out two weeks after the seeding. Then, the two leaves were put into a 1.5 ml Eppendorf tube and were pestled. 100 µl of DNA extraction solution (including 200 mM Tris/HCl at pH 7.5, 250 mM NaCl, 2.5 mM EDTA at pH 8.0, and 0.5% SDS) was added therein and the solution thus prepared was stirred well therein. Then, the solution thus prepared was centrifuged at 10,080×g for 10 minutes. After that, 80 µl of the resulting supernatant was transferred into a new 1.5 ml Eppendorf tube, and 60 µl of isopropanol was added therein and the solution thus prepared was stirred therein. Then, the solution thus obtained was centrifuged at 10,080×g for 10 minutes. After that, the resulting supernatant was discarded, and 200 µl of 70% ethanol was added therein and the mixture thus obtained was stirred well. Subsequently, the mixture was centrifuged at 10,080×g for 5 minutes, and then the resulting supernatant was discarded and the pellet was vacuum-dried (TOMY Micro Vac) for 15 minutes. Then, the dried pellet was dissolved in 20 µl of TE, and the resultant solution was centrifuged at 10,080×g for 10 minutes. The resulting supernatant was used as a template for PCR. The PCR was carried out with a PCR reaction solution containing: 2 µl of 25 mM MgCl2; 2 µl of 10×PCR buffer; 0.5 µl of 10 mM dNTP; 0.15 µl of Sigma Taq DNA polymerase; 1.0 µl of template DNA solution; 1.0 µl of primer1; 1.0 µl of primer2; and 12.35 µl of H2O. The PCR was carried out in 25 cycles (94° C. for 30 seconds, 60° C. for 60 seconds, and 72° C. for 120 seconds). The PCR was carried out with two combinations of the primers: (i) the primer F-1 and the primer F-2; and (ii) the primer F-1 and the primer T-1. Following the PCR, 1.2% agarose gel electrophoresis was carried out, so that an individual in which a band was observed only for the combination of (ii) the primer F-1 and the primer T-1 was obtained as a homogenous T-DNA inserted mutant of FBA1. Hereafter, this T-DNA inserted mutant of FBA1 is referred to as "049B07".

(4) A *Colletotrichum higginsianum* Inoculation Experiment 1

*Colletotrichum higginsianum*, whose host plant was a cruciferous plant, was used as a sample fungus. The *Colletotrichum higginsianum* was cultured on a PDA slant medium at 22° C. for 10 days, and then spores thus obtained were collected by using an inoculation loop. The spores were suspended in sterilized water, so as to obtain a spore suspension, which was then adjusted to 1×105 spore/ml.

10 μl of the spore suspension was spotted to two points each on a leaf of each type of *Arabidopsis thaliana* (Col-0, 35S-FBA1/Col-0, cad2-1, 35S-FBA1/cad2-1, and 049B07) at the age of 4 weeks. Pots in which each plant was grown were placed on trays, and which were covered with a transparent plastic cover so that sufficient humidity was maintained therein. Then, these plants were incubated at 22° C. under the long day condition for 6 days.

The leaves inoculated with *Colletotrichum higginsianum* were photographed 6 days after the inoculation, and stained with trypan blue so as to stain cells necrotized because of infection, in accordance with a method by Koch and Slusarenko (Koch, E. and Slusarenko, A. (1990) *Arabidopsis* is susceptible to infection by a downy mildew fungus. Plant Cell 2, 437-445). That is, the leaf inoculated with *Colletotrichum higginsianum* was immersed into a Lactophenol-trypan blue solution (including 10 ml of lactic acid, 10 ml of glycerol, 10 g of phenol, and 10 mg of trypan blue in 10 ml water) diluted by ½ with ethanol. The leaf was then boiled for 3 minutes. After that, the leaf was washed with 2.5 g/ml of chloral hydrate (Wako, Tokyo, Japan).

Figure 4:
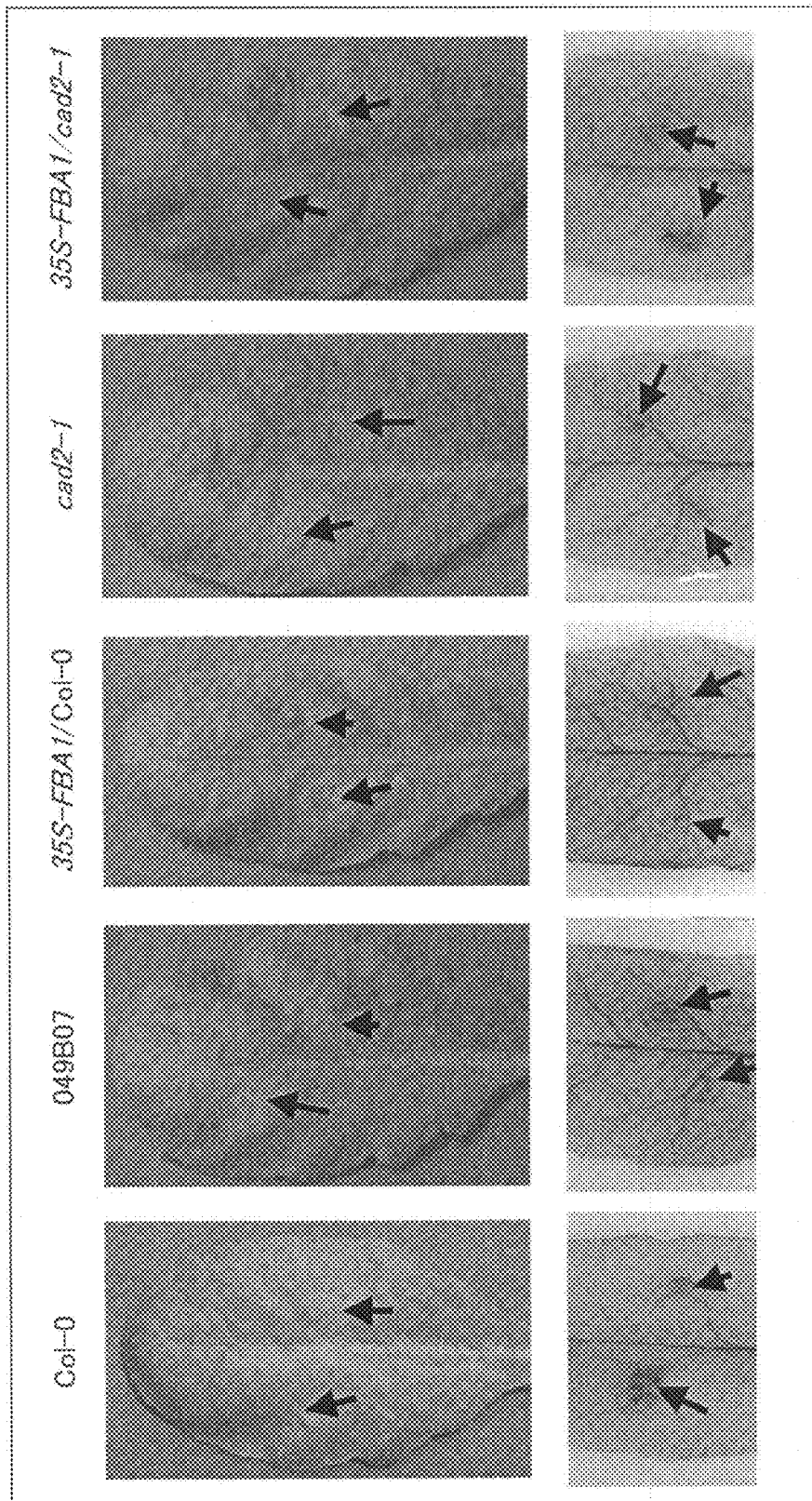
FIG. 4 shows: photographs of leaves of five types of *Arabidopsis thaliana* (Col-0, 35S-FBA1/Col-0, cad2-1, 35S-FBA1/cad2-1, and 049B07) inoculated with spores of *Colletotrichum higginsianum* (in the upper part); and photographs of the leaves stained with trypan blue (in the lower part).

FIG. 4 shows the result. The photographs in the upper part in FIG. 4 are of the leaves inoculated with *Colletotrichum higginsianum*, and the photographs in the lower part in FIG. 4 are of the leaves inoculated with *Colletotrichum higginsianum* and stained with trypan blue. The arrows in FIG. 4 indicate the inoculated points. As is clear from FIG. 4, the inoculated points of Col-0 (wild type) had been necrotized (stained dark blue by the trypan blue staining). However, in the inoculated points of the transformed plant (35S-FBA1/Col-0), necrotized portions were hardly recognized. On the other hand, in the inoculated points of 35S-FBA1/cad2-1 which was produced by introducing FBA1 into cad2-1, the introduction of 35S-FBA1 was not effective and necrotized portions were recognized.

Figure 5:
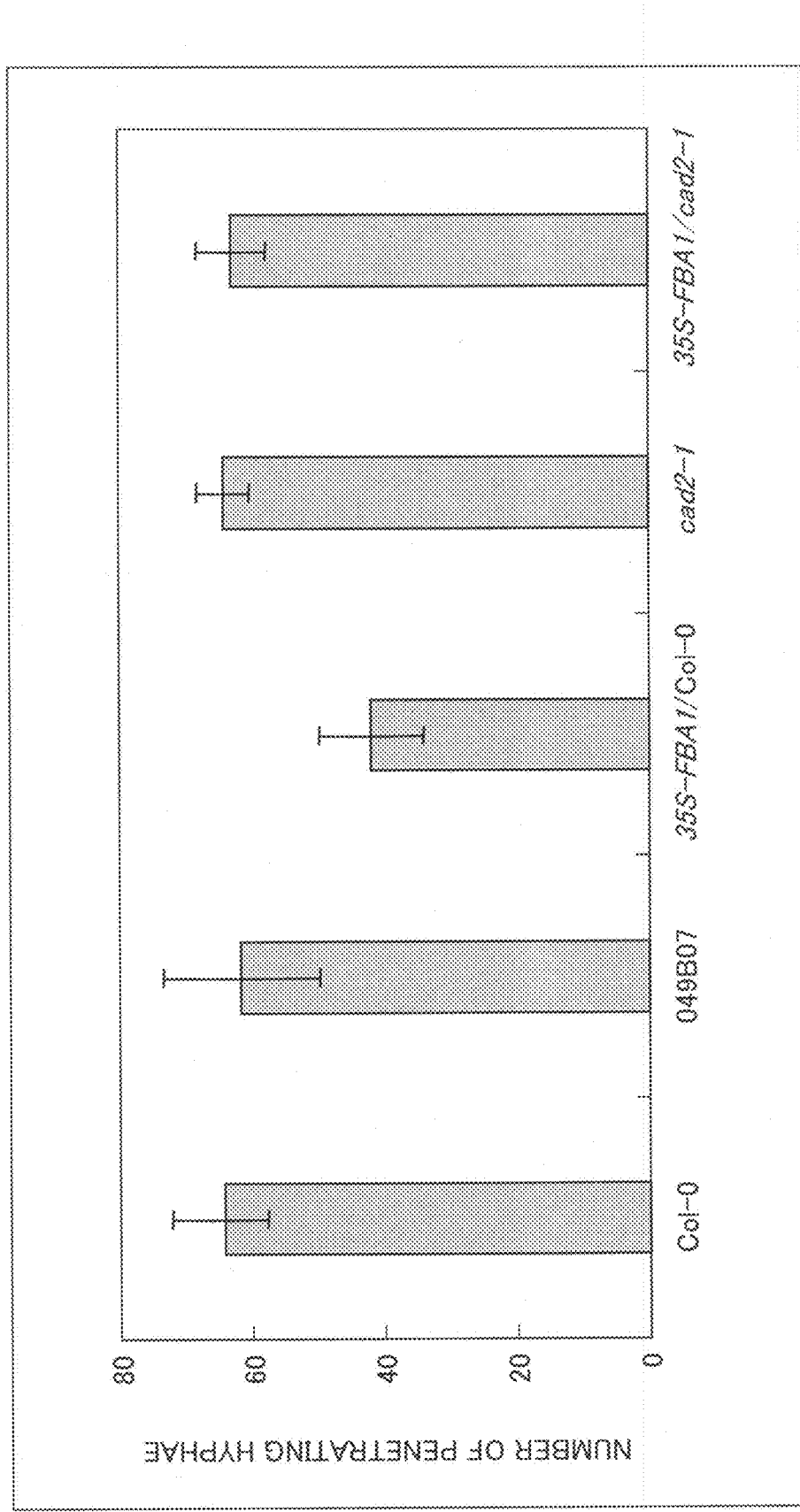
FIG. 5 is a graph illustrating the number of hyphae penetrated to leaves of five types of *Arabidopsis thaliana* (Col-0, 35S-FBA1/Col-0, cad2-1, 35S-FBA1/cad2-1, and 049B07) inoculated with spores of *Colletotrichum higginsianum*.

After the trypan blue staining, the number of spores and the number of spores having penetrating hyphae were counted by using an optical microscope. FIG. 5 shows the result. The result clearly shows that 35S-FBA1/Col-0 had a fewer number of penetrating hyphae, compared with the plants of other lines.

Figure 6:
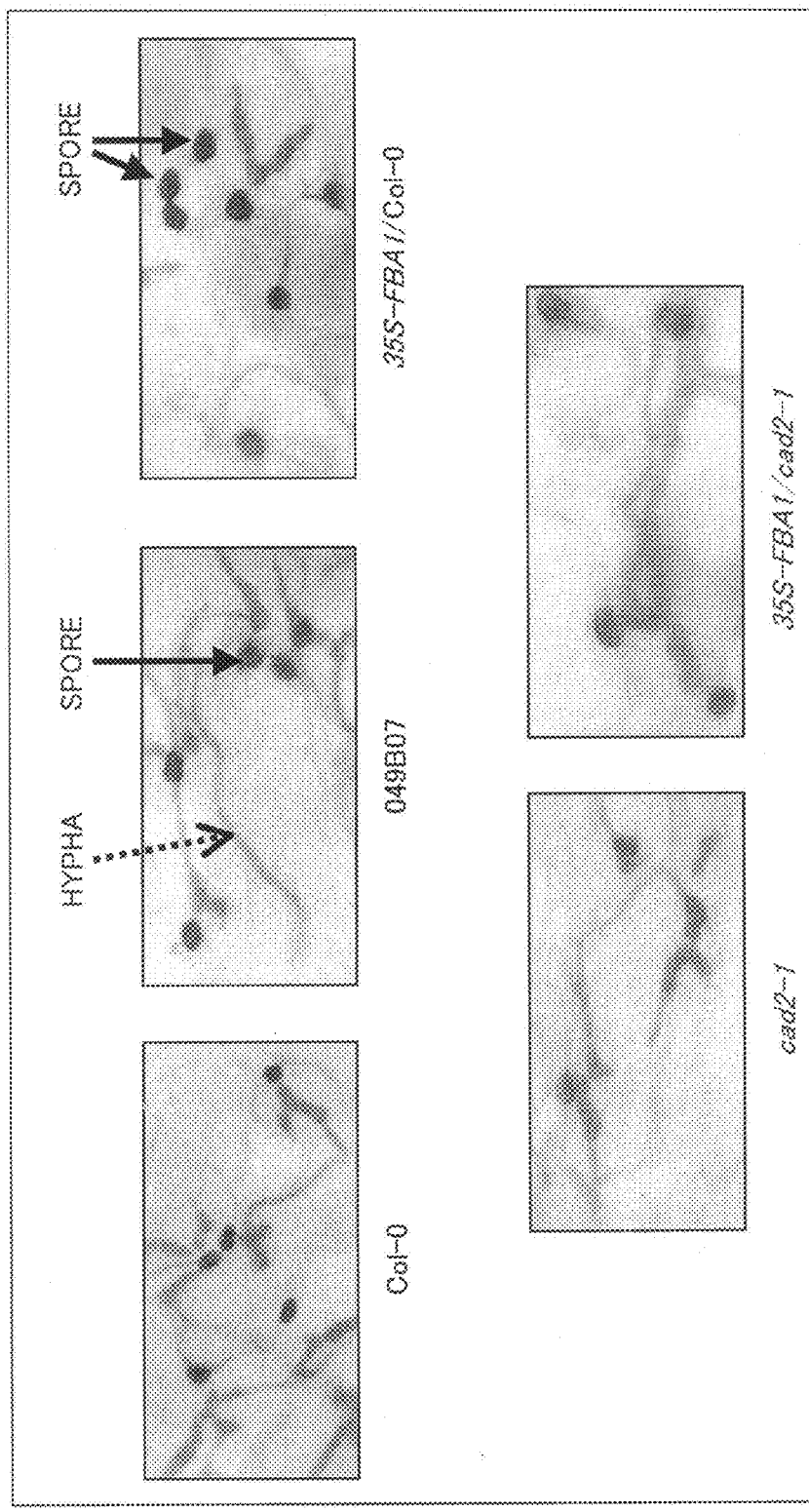
FIG. 6 shows micrographs for observing penetrating hyphae by carrying out trypan blue staining on leaves of five types of *Arabidopsis thaliana* (Col-0, 35S-FBA1/Col-0, cad2-1, 35S-FBA1/cad2-1, and 049B07) inoculated with spores of *Colletotrichum higginsianum*.

Further, after the trypan blue staining, the photographs of the penetrating hyphae were taken by using the optical microscope (×250). FIG. 6 shows the photographs thus taken. The photographs clearly shows that 35S-FBA1/Col-0 had a shorter length of penetrating hyphae and a fewer number of penetrating hyphae, compared with the plants of other lines.

(5) A *Colletotrichum higginsianum* Inoculation Experiment 2

A spore suspension (concentration: 1×10² spore/ml) of *Colletotrichum higginsianum* was prepared in the same manner as in (4).

The spore suspension was sprayed and inoculated onto five types of *Arabidopsis thaliana* (Col-0, 35S-FBA1/Col-0, cad2-1, 35S-FBA1/cad2-1, and 049B07) at the age of 4 weeks. Pots in which each plant was grown were placed on trays, and which were covered with a transparent plastic cover so that sufficient humidity was maintained. Then, these plants were incubated at 22° C. under the long day condition for 24 days.

Figure 7:
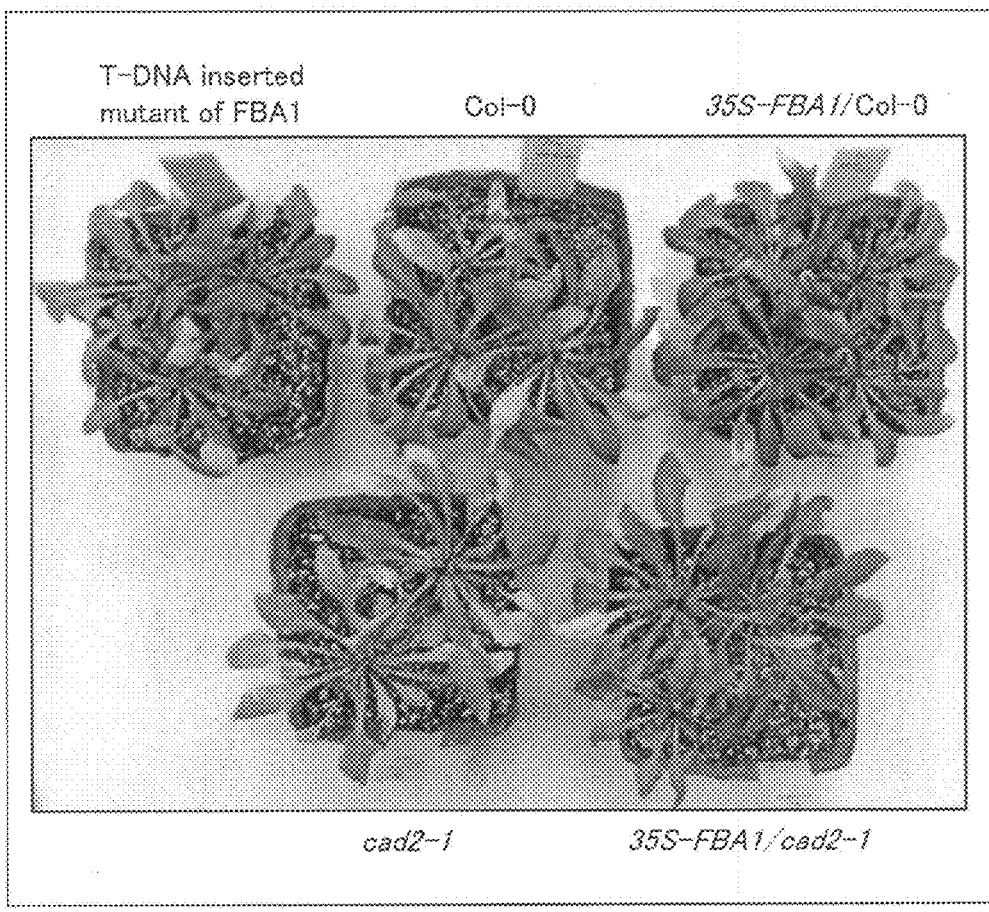
FIG. 7 shows a photograph of five types of *Arabidopsis thaliana* (Col-0, 35S-FBA1/Col-0, cad2-1, 35S-FBA1/cad2-1, and 049B07) inoculated with spores of *Colletotrichum higginsianum*, the photograph having been taken 24 days after the inoculation.

FIG. 7 shows the photograph of the plants of each line, the photograph having been taken 24 days after the inoculation. FIG. 7 clearly shows the followings: (i) in 35S-FBA1/Col-0, although the leaves infected with *Colletotrichum higginsianum* by the spray carried out in an early stage of this experiment had been necrotized, new leaves were formed and no further infection did not occur; (ii) on the other hand, in the plants of other lines, almost all of the leaves had been necrotized, and infection had spread to new leaves which were formed.

(6) A *Pseudomonas syringae* pv. Tomato Strain DC3000 Inoculation Experiment

The resistance to plant pathogenic fungi was investigated by using *Pseudomonas syringae* pv. tomato strain DC3000. It is known that the *Pseudomonas syringae* pv. tomato strain DC3000 is a plant pathogenic fungus that can infect *Arabidopsis thaliana*. The *Pseudomonas syringae* pv. tomato strain DC3000 from a glycerol stock (−80° C.) was inoculated by streaking onto a KB agar medium (including 20 g of proteose peptone No. 3; 1.4 g of K2HPO4; 0.4 g of MgSO4.7H2O; and 10 ml/L of glycerol), and was cultured at 28° C. for 2 days. Then, the cells were collected by using a Cell Scraper (Asahi Techno Glass, Funahashi, Chiba, Japan). The cells were suspended in an appropriate amount of 10 mM MgCl2 solution, so as to obtain a suspension, which was then adjusted to 10⁸ cfu/ml. The suspension was sprayed and inoculated onto five types of *Arabidopsis thaliana* (Col-0, 35S-FBA1/Col-0, cad2-1, 35S-FBA1/cad2-1, and 049B07) at the age of 4 weeks. Then, these plants were incubated at 22° C. under the long day condition.

Figure 8:
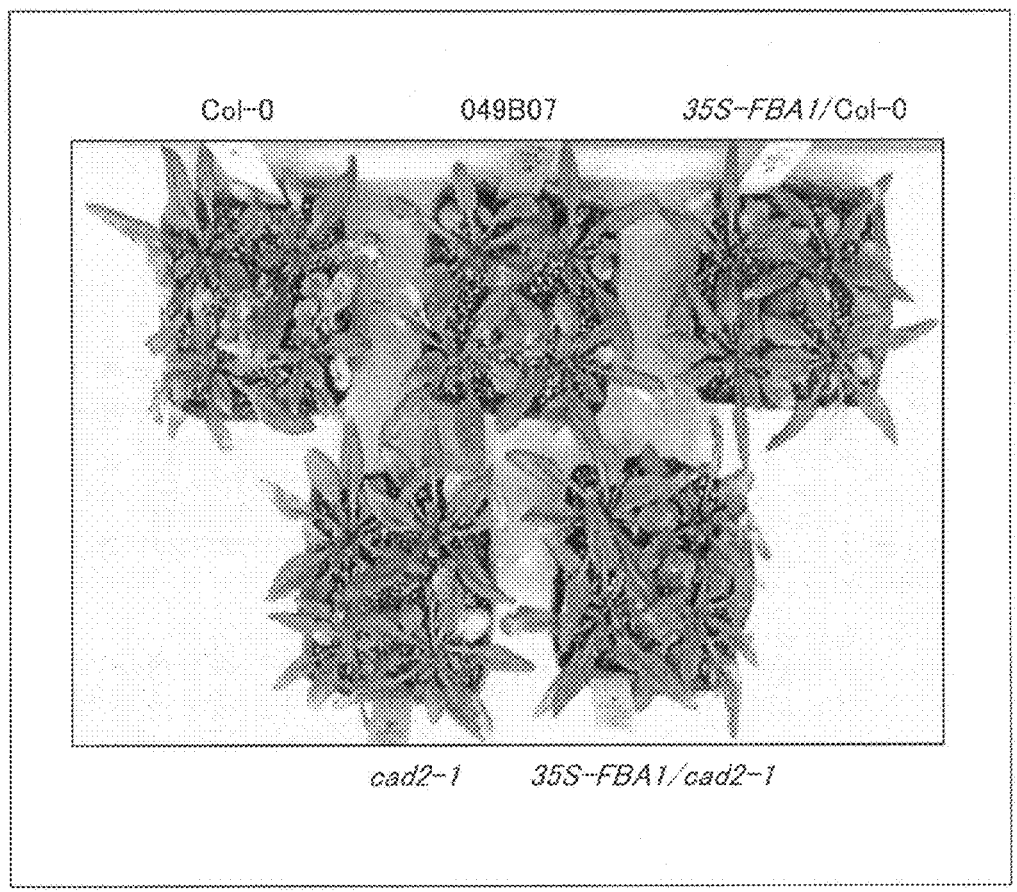
FIG. 8 shows a photograph of five types of *Arabidopsis thaliana* (Col-0, 35S-FBA1/Col-0, cad2-1, 35S-FBA1/cad2-1, and 049B07) inoculated with spores of *Pseudomonas syringae* pv. tomato strain DC3000, the photograph having been taken 5 days after the inoculation.

FIG. 8 shows the result. As is clear from FIG. 8, 35S-FBA1/Col-0 had a notably fewer number of the leaves which were necrotized, compared with the plants of other lines. Regarding a plant into which FBA1 is to be introduced (i.e., a host plant), the following should be noted. When FBA1 was introduced into cad2-1, the effectiveness of the introduction was reduced, compared with a case FBA1 is introduced into Col-0. Therefore, it is apparent the effectiveness of the introduction of FBA1 increases when FBA1 is introduced into a plant of the line having a higher glutathione synthetic capacity.

(7) Salicylate Treatment 1 mM salicylate was sprayed onto five types of *Arabidopsis thaliana* (Col-0, 35S-FBA1/Col-0, cad2-1, 35S-FBA1/cad2-1, and 049B07) at the age of 4 weeks, and a transparent plastic cover was used for covering so that humidity was maintained. The salicylate is a signal substance synthesized inside a plant when the plant is infected with germs (especially pathogenic bacteria), for the purpose of reaction for controlling the incidence caused by pests including insects and diseases. PR1 is an antibacterial protein whose expression is controlled by a signal of the salicylate.

Following the spray, three leaves were picked from every plant. Specifically, one leaf was picked 6 hours after the spray, another leaf was picked 12 hours after the spray, and the other leaf was picked 24 hours after the spray. Then, the leaves were immobilized by using liquid nitrogen. RNA from each leaf was purified. Then, a cDNA was produced from an equal amount of 18S rRNA derived from each RNA. With a reaction solution containing: 7.5 μl of premix EX-taq (TaKaRa, Shiga, Japan); 2 μl of PR1-F primer (1.33 μM); 2 μl of PR1-R primer (1.33 μM); 2 μl of cDNA template (0.025 μg); and 1.5 μl of H2O, RT-PCR was carried out in 30 cycles (94° C. for 30 seconds, 58° C. for 60 seconds, and 72° C. for 60 seconds).

The primers used are as follows:

```
                                          (SEQ ID NO: 22)
PR1-F:    5'-CAGCCCCAAGACTACTTCAATGC-3'

(SEQ ID NO: 23)
PR1-R:    5'-GGTCGTTCAATAAGAATGACAGACG-3'
```

The PCR products were subjected to 1.2% agarose gel electrophoresis, and measured quantitatively by using Bio-Analyzer (Agilent Technologies, Germany). FIG. 9(*a*) and FIG. 9(*b*) show the result. FIG. 9(*a*) shows the result of the electrophoresis, and FIG. 9(*b*) shows the relative amount of PR1 mRNA. As is clear from FIG. 9(*a*) and FIG. 9(*b*), 35S-FBA1/Col-0 maintained a higher expression level of a PR1 gene even after 24 hours had passed since the salicylate treatment was performed, compared with the plants of other lines.

Regarding a plant into which FBA1 is to be introduced (i.e., a host plant), the following should be noted. When FBA1 was introduced into cad2-1, the effectiveness of the introduction was reduced, compared with a case FBA1 was introduced into Col-0. Therefore, it is apparent that the effectiveness of the introduction of FBA1 increases when FBA1 is introduced into a plant of the line having a higher glutathione synthetic capacity.

(8) Jasmonate Treatment

50 µM jasmonate was sprayed onto five types of *Arabidopsis thaliana* (Col-0, 35S-FBA1/Col-0, cad2-1, 35S-FBA1/cad2-1, and 049B07) at the age of 4 weeks, and a transparent plastic cover was used for covering so that humidity was maintained. It is known that the jasmonate is a signal substance synthesized inside a plant when the plant is infected with pathogenic microorganism (especially mycete) or subjected to feeding damage caused by insects, for the purpose of defense reaction against the incidence caused by disease or insects. PDF1.2 is an antifungal protein whose expression is controlled by a signal of the jasmonate.

Following the spray, three leaves were picked from every plant. Specifically, one leaf was picked 6 hours after the spray, another leaf was picked 12 hours after the spray, and the other leaf was picked 24 hours after the spray. Then, the leaves were immobilized by using liquid nitrogen. RNA from each leaf was purified. Then, a cDNA was produced from an equal amount of 18S rRNA derived from each RNA. After that, reaction solution containing: 7.5 µl of premix EX-taq (TaKaRa, Shiga, Japan); 2 µl of PDF1.2-F primer (1.33 µM); 2 µl of PDF1.2-R primer (1.33 µM); 2 µl of cDNA template (0.025 µg); and 1.5 µl of H2O was prepared, and RT-PCR was carried out in 27 cycles (94° C. for 30 seconds, 58° C. for 60 seconds, and 72° C. for 60 seconds).

The primers used for amplifying the PDF1.2 are as follows:

```
                                     (SEQ ID NO: 24)
PDF1.2-F: 5'-TAAGTTTGCTTCCATCATCACCC-3'

(SEQ ID NO: 25)
PDF1.2-R: 5'-GTGCTGGGAAGACATAGTTGCAT-3'
```

As well as in (5) above, the PCR products were subjected to 1.2% agarose gel electrophoresis, and measured quantitatively by using the Bio-Analyzer. FIG. 10(a) and FIG. 10(b) show the result. FIG. 10(a) shows the result of the electrophoresis, and FIG. 10(b) shows the relative amount of PDF1.2 mRNA. As is clear from FIG. 10(a) and FIG. 10(b), 35S-FBA1/Col-0 had a higher expression level of a PDF1.2 gene 24 hours after the jasmonate processing, compared with the plants of other lines. Regarding a plant into which FBA1 is to be introduced (i.e., a host plant), the following should be noted. When FBA1 was introduced into cad2-1, the effectiveness of the introduction was reduced, compared with a case FBA1 was introduced into Col-0. Therefore, it is apparent that the effectiveness of the introduction of FBA1 increases when FBA1 is introduced into a plant of the line having a higher glutathione synthetic capacity.

(9) Plant Growth Traits

[9-1] Comparison Between a Transformed Plant (35S-FBA1/Col-0) and a Wild-Type Plant (Col-0)

It was observed that transformed *Arabidopsis thaliana* (35S-FBA1/Col-0) into which an FBA1 gene was introduced had significantly improved plant growth traits, compared with wild-type *Arabidopsis thaliana* (Col-0).

Figure 11:
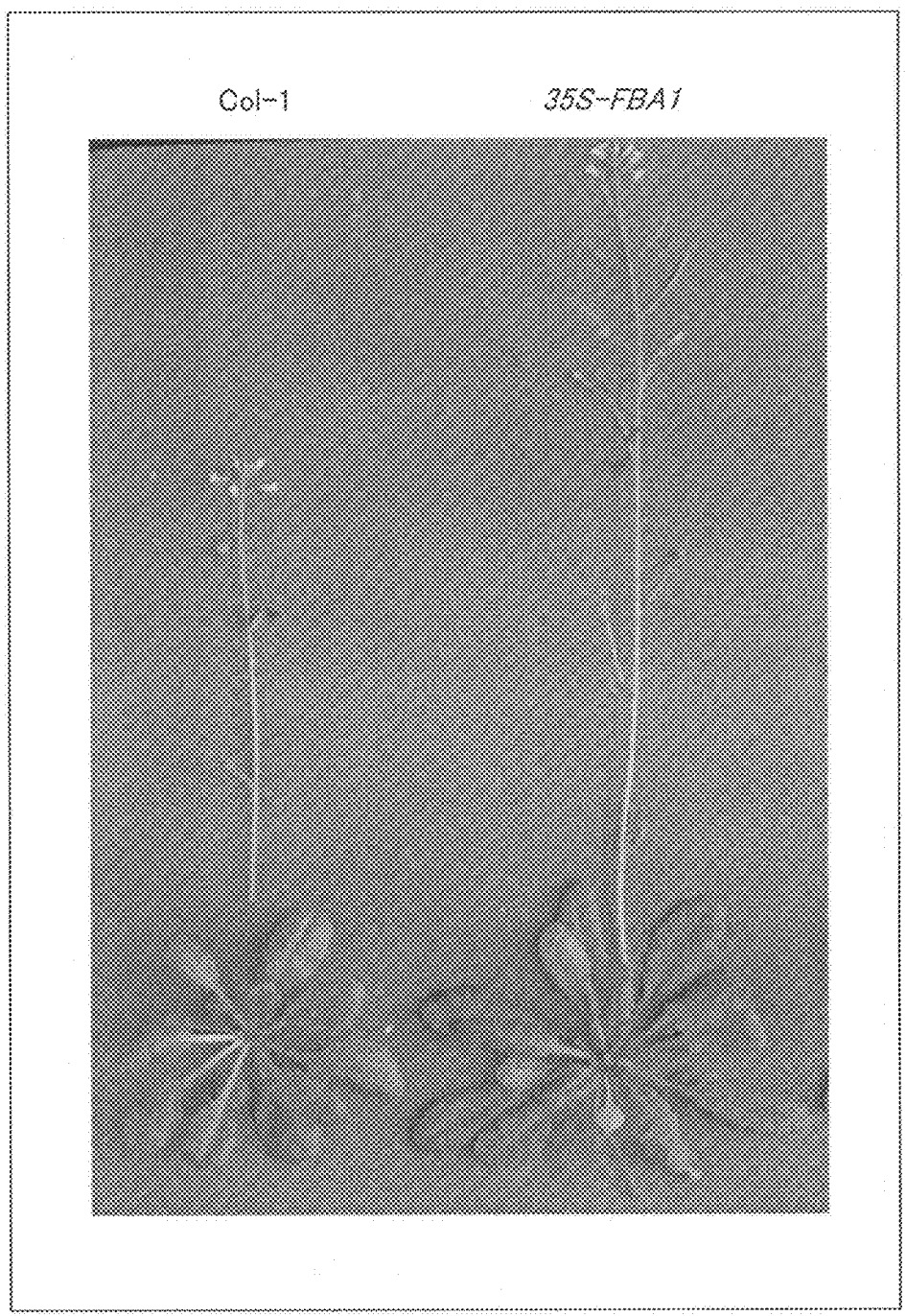
FIG. 11 shows a photograph of wild-type *Arabidopsis thaliana* (Col-1) and transformed *Arabidopsis thaliana* (35S-FBA1/Col-0) into which an FBA1 gene was introduced, the photograph having been taken 42 days after seeding.

FIG. 11 shows a photograph comparing between Col-0 and 35S-FBA1/Col-0, each of Col-0 and 35S-FBA1/Col-0 being at the age of 6 weeks. This clearly shows that 35S-FBA1/Col-0 is larger than Col-0.

[9-2] Plant Growth Traits of a Transformed Plant into which an Amino Acid-Substituted FBA1 is Introduced In order to clarify the importance of a cysteine residue contained in an amino acid sequence of FBA1 (SEQ ID NO: 1), four types of *Arabidopsis thaliana* (35S-fba1C72A, 35S-fba1C128A, 35S-fba1C156A, and 35S-fba1C187A) were produced so that they expressed enzymes in which different cysteine residues were substituted with an alanine residue, in accordance with the procedures described in (2) above (for example, "C72A" represents the introduction of a construct expressing an FBA1 enzyme in which cysteine in position 72 of SEQ ID NO: 1 has been substituted with alanine).

Figure 12:
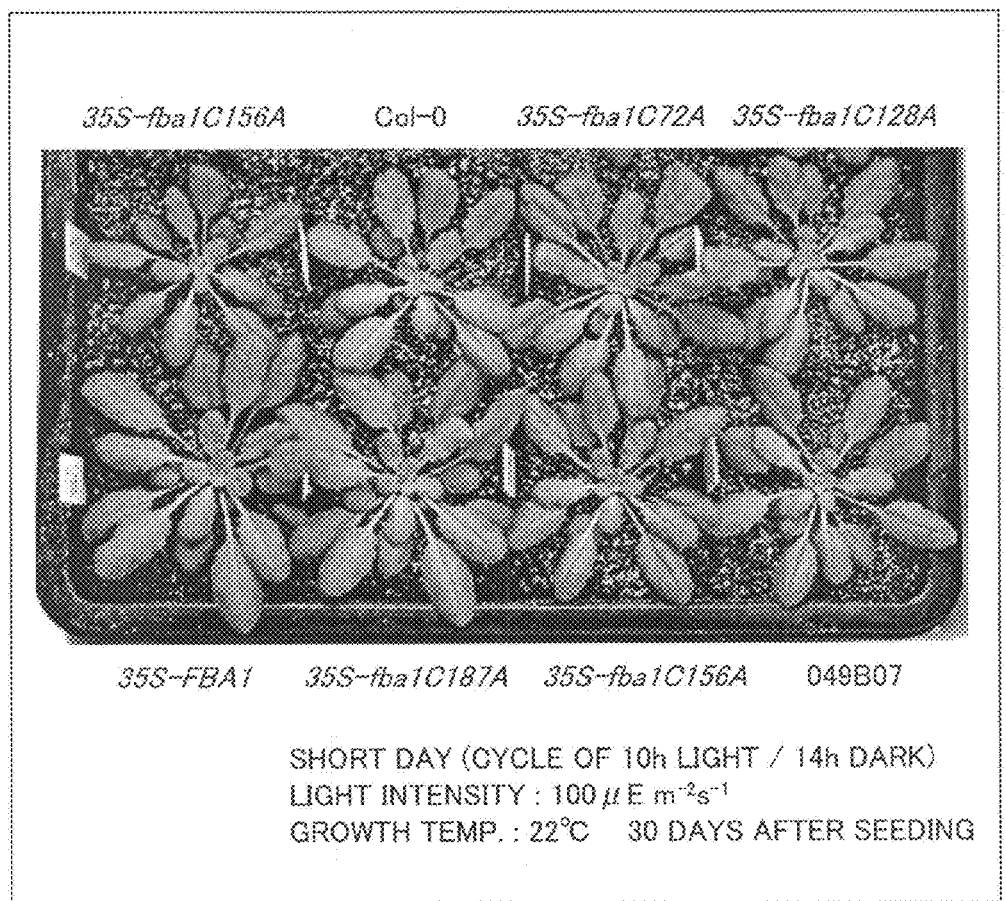
FIG. 12 shows a photograph of: wild type *Arabidopsis thaliana* (Col-1); a T-DNA insertion mutant of an FBA1 gene (049B07); transformed *Arabidopsis thaliana* into which an FBA1 gene was introduced (35S-FBA1/Col-0); and four types of transformed *Arabidopsis thaliana* into which four types of FBA1 genes mutated to encode FBA1s with different one of cysteine residues substituted with an alanine residue were introduced respectively, the photograph having been taken 30 days after seeding.
Figure 13:
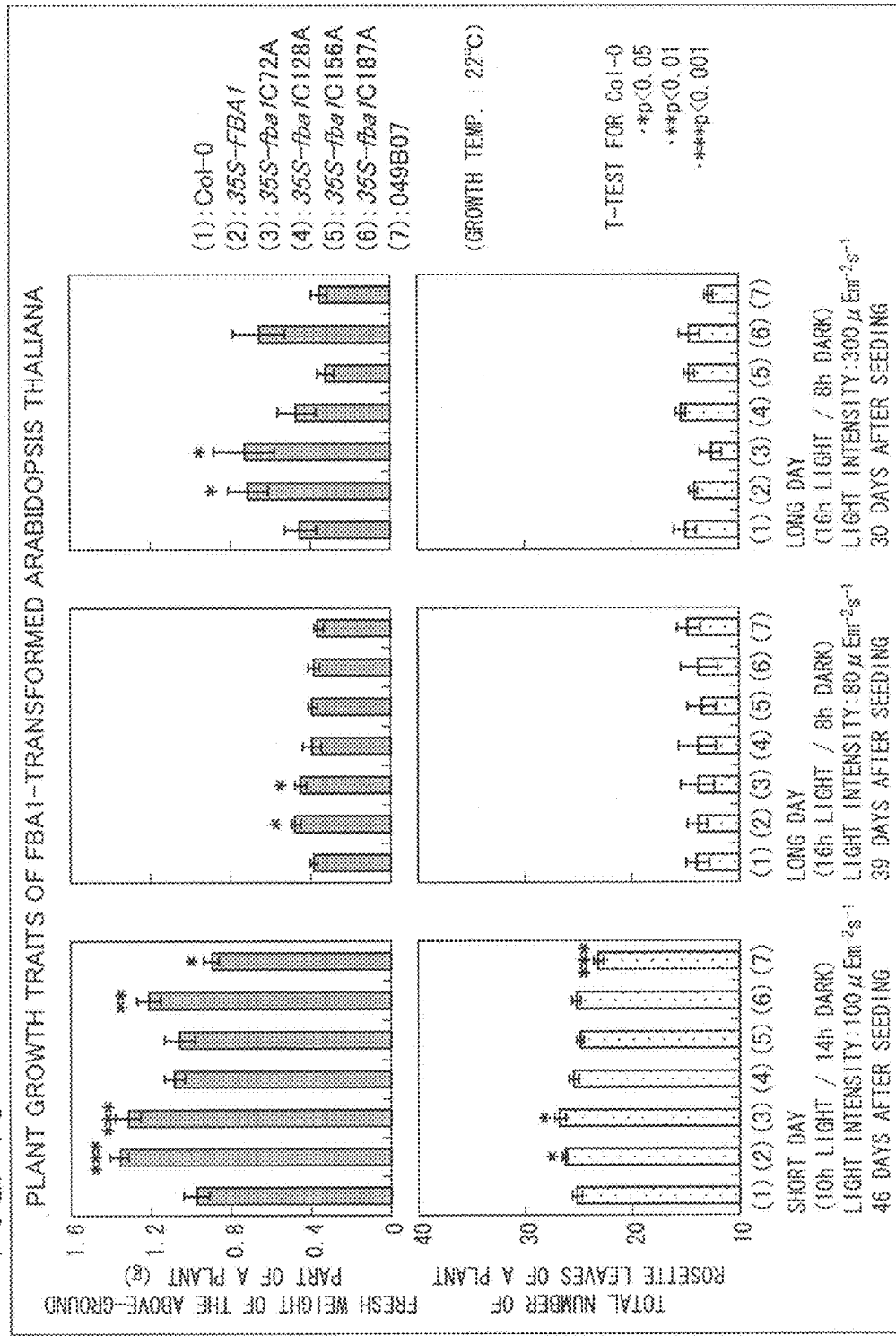
FIG. 13 shows graphs comparing, the following types of *Arabidopsis thaliana* in (i) fresh weight of the above-ground part of a plant and in (ii) the total number of rosette leaves of a plant, between: wild type *Arabidopsis thaliana* (Col-1); a T-DNA inserted mutant of an FBA1 gene (049B07); transformed *Arabidopsis thaliana* into which an FBA1 gene was introduced (35S-FBA1/Col-0); and four types of transformed *Arabidopsis thaliana* into which four types of FBA1 genes mutated to encode FBA1s with different one of cysteine residues substituted with an alanine residue were introduced respectively.

FIG. 12 shows a photograph of the plants 30 days after seeding. FIG. 13 shows a graph comparing between the plants in (i) fresh weight of the above-ground part of a plant and in (ii) the total number of rosette leaves of a plant. As is clear from FIG. 12 and FIG. 13, 35S-fba1C72A and 35S-fba1C187A had more improved plant growth traits as well as 35S-FBA1/Col-0 did, compared with a wild type (Col-0). On the other hand, 35S-fba1C128A and 35S-fba1C156A exhibited similar plant growth traits to the plant growth traits of the wild type (Col-0), although the effectiveness was different between the three depending on the light intensity during plant growth. According to this result, such a possibility was suggested that the cysteine playing an important role for the function of FBA1 was the cysteine of position 128 and the cysteine of position 156 in SEQ ID NO: 1. When the cysteine of position 72 and the cysteine of position 187 were substituted with another amino acid respectively, the plant growth traits were improved. Thus, the following fact was exemplified: the plant growth traits could be improved even in a plant in which a gene mutated to encode FBA1 with an original amino acid substituted with another amino acid in an amino acid sequence of FBA1 was introduced.

Further, as is clear from FIG. 13, the plant in which the plant growth traits were improved revealed an increase in the total number of rosette leaves thereof. This indicated that a growing speed of the plant could be increased by introduction of an FBA1 gene, as well as the extent of growth of a plant.

[9-3] Confirmation of Improvement in CO2 Fixation Ability

Figure 14:
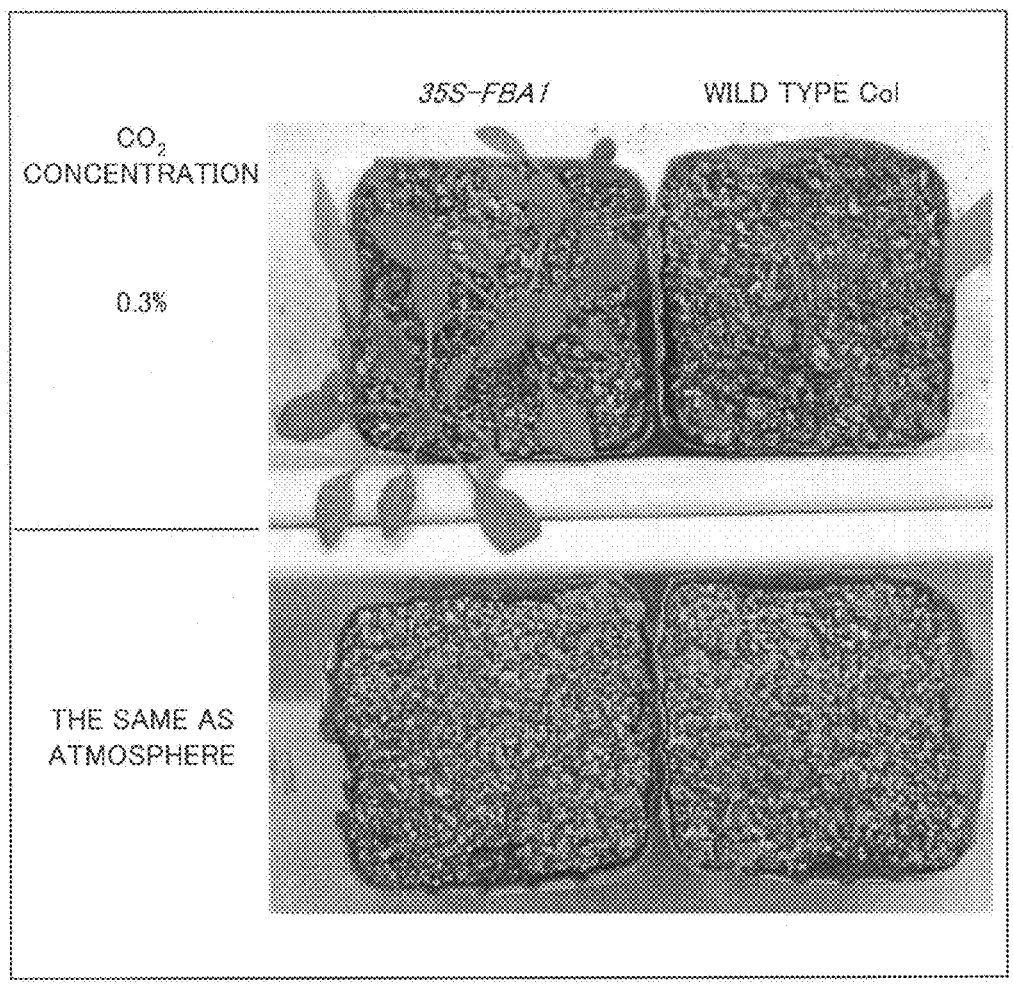
FIG. 14 shows a photograph of: wild-type *Arabidopsis thaliana* (Col-1); and transformed *Arabidopsis thaliana* (35S-FBA1) into which an FBA1 gene was introduced, each of which was grown up (a) under the same CO2 condition as in the atmosphere and (b) under a high CO2 condition, the photograph having been taken 25 days after seeding.

In order to examine whether or not potential CO2 fixation ability of a 35S-FBA1 plant was improved, comparison was made between (i) plants grown up at CO2 concentration controlled to 0.3% and (ii) plants grown up at atmospheric CO2 concentration. FIG. 14 and FIG. 15 show the result. As shown in FIG. 14 and FIG. 15, in the case of a wild-type plant (Col-0), its plant growth traits were improved along with the increase in CO2 concentration; on the other hand, in the case of the 35S-FBA1 plant, its plant growth traits were improved significantly along with the increase in CO2 concentration. This result indicates that CO2 fixation ability of a plant can be significantly enhanced by introduction of an FBA1 gene.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

All of the academic documents and the patent documents in the present specification are as reference to the present specification.

INDUSTRIAL APPLICABILITY

The present invention provides a plant in which plant growth traits are improved and the incidence caused by pests including insects and diseases is controlled. Therefore, the present invention is expected to be applicable to agriculture and forestry.

The invention claimed is:

1. A method for producing a plant in which plant growth traits are improved and damage caused by insects or diseases are reduced, the method comprising the steps of:
  introducing, to a plant, a DNA encoding a glutathione-binding plastid-type fructose-1,6-bisphosphate aldolase, and
  selecting a plant transformed with the DNA encoding the glutathione-binding plastid-type fructose-1,6-bisphosphate aldolase and exhibiting improved insect-resistance or improved disease resistance.

2. The method as set forth in claim 1,
  wherein the DNA encoding the glutathione-binding plastid-type fructose-1,6-bisphosphate aldolase is selected from the group consisting of the following (a) through (d):
  (a) a DNA encoding a protein having the amino acid sequence shown in SEQ ID NO: 1;
  (b) a DNA encoding a protein having an amino acid sequence with deletion, substitution, or addition of 10 or less amino acids in the amino acid sequence shown in SEQ ID NO: 1;
  (c) a DNA having the base sequence shown in SEQ ID NO: 2; and
  (d) a DNA that hybridizes under stringent conditions with a DNA having the base sequence shown in SEQ ID NO: 2.

3. The method as set forth in claim 1, wherein the one or more selected plants exhibits improved resistance to an insect.

4. The method as set forth in claim 1, wherein the one or more selected plants exhibits improved resistance to a disease.

5. The method as set forth in claim 4, wherein the one or more selected plants exhibits improved resistance to *Colletotrichum higginsianum* infection.

6. The method as set forth in claim 4, wherein the one or more selected plants exhibits improved resistance to *pseudomonas syringae* infection.

* * * * *

SEQUENCE LISTING

<160> NUMBER OF SEQ ID NOS: 25

<210> SEQ ID NO 1
<211> LENGTH: 391
<212> TYPE: PRT
<213> ORGANISM: Arabidopsis thaliana

<400> SEQUENCE: 1

```
Met Ala Ser Ala Ser Phe Val Lys Pro Asn Thr Leu Ser Ser Pro Trp
  1               5                  10                  15

Ile Gly Gln Arg Ser Phe Ala His Thr Ser Ala Ser Ser Pro Pro
                 20                  25                  30

Pro Arg Val Ser Phe Ala Ile Arg Ala Gly Ala Tyr Ser Asp Glu Leu
             35                  40                  45

Val Lys Thr Ala Lys Ser Ile Ala Ser Pro Gly Arg Gly Ile Leu Ala
 50                  55                  60

Ile Asp Glu Ser Asn Ala Thr Cys Gly Lys Arg Leu Ala Ser Ile Gly
 65                  70                  75                  80

Leu Asp Asn Thr Glu Asp Asn Arg Gln Ala Tyr Arg Gln Leu Leu Leu
                 85                  90                  95

Thr Thr Pro Gly Leu Gly Asp Tyr Ile Ser Gly Ser Ile Leu Phe Glu
            100                 105                 110

Glu Thr Leu Tyr Gln Ser Thr Lys Asp Gly Lys Thr Phe Val Asp Cys
            115                 120                 125

Leu Arg Asp Ala Asn Ile Val Pro Gly Ile Lys Val Asp Lys Gly Leu
130                 135                 140

Ser Pro Leu Ala Gly Ser Asn Glu Glu Ser Trp Cys Gln Gly Leu Asp
145                 150                 155                 160

Gly Leu Ala Ser Arg Ser Ala Glu Tyr Tyr Lys Gln Gly Ala Arg Phe
                165                 170                 175

Ala Lys Trp Arg Thr Val Val Ser Val Pro Cys Gly Pro Ser Ala Leu
            180                 185                 190

Ala Val Lys Glu Ala Ala Trp Gly Leu Ala Arg Tyr Ala Ala Ile Ser
            195                 200                 205

Gln Asp Asn Gly Leu Val Pro Ile Val Glu Pro Glu Ile Leu Leu Asp
210                 215                 220

Gly Asp His Pro Ile Glu Arg Thr Leu Glu Val Ala Glu Lys Val Trp
225                 230                 235                 240

Ser Glu Val Phe Phe Tyr Leu Ala Gln Asn Asn Val Met Phe Glu Gly
                245                 250                 255

Ile Leu Leu Lys Pro Ser Met Val Thr Pro Gly Ala Glu His Lys Asn
            260                 265                 270

Lys Ala Ser Pro Glu Thr Val Ala Asp Phe Thr Leu Thr Met Leu Lys
            275                 280                 285

Arg Arg Val Pro Pro Ala Val Pro Gly Ile Met Phe Leu Ser Gly Gly
        290                 295                 300

Gln Ser Glu Ala Glu Ala Thr Leu Asn Leu Asn Ala Met Asn Gln Ser
305                 310                 315                 320

Pro Asn Pro Trp His Val Ser Phe Ser Tyr Ala Arg Ala Leu Gln Asn
                325                 330                 335

Ser Val Leu Arg Thr Trp Gln Gly Lys Pro Glu Lys Ile Glu Ala Ser
            340                 345                 350

Gln Lys Ala Leu Leu Val Arg Ala Lys Ala Asn Ser Leu Ala Gln Leu
            355                 360                 365
```

-continued

Gly Lys Tyr Ser Ala Glu Gly Glu Asn Glu Asp Ala Lys Lys Gly Met
        370                 375                 380

Phe Val Lys Gly Tyr Thr Tyr
385                 390

<210> SEQ ID NO 2
<211> LENGTH: 1176
<212> TYPE: DNA
<213> ORGANISM: Arabidopsis thaliana

<400> SEQUENCE: 2

| | | | |
|---|---|---|---|
| atggcgtctg ctagcttcgt taagcctaac accctctctt ctccatggat cggccaacgc | 60 |
| tcctttgctc acacctctgc ttcttcttct cctcctcctc gagtctcctt cgcgatccgc | 120 |
| gccggtgctt actccgacga gcttgttaaa accgccaaaa gcattgcatc ccctgggaga | 180 |
| ggtatcttgg cgatcgatga gtccaatgca acctgtggga agaggcttgc ttctatcggc | 240 |
| ttggataaca ccgaggacaa ccgtcaggcc tacaggcaac ttctgcttac cactcctggc | 300 |
| ctcggcgatt acatctctgg ttccattctc ttcgaggaga ctctttacca gtccaccaag | 360 |
| gacggtaaga ccttttgtcga ttgcttgcgc gatgccaaca tcgtccctgg catcaaagtt | 420 |
| gacaagggct tgtctcccct agccggttcc aacgaagagt cttggtgcca aggcttggat | 480 |
| ggattggcct cacgctctgc tgagtactac aagcaaggcg ctcgttttgc caagtggagg | 540 |
| acagtggtga gtgttccctg cggtccttca gcactggctg tgaaggaagc tgcgtggggg | 600 |
| ctggctcgct atgcagccat ctctcaggat aatggtcttg tccccattgt ggagccagag | 660 |
| atccttctgg acggggacca cccaatagag aggactctgg aggtggcaga gaaagtgtgg | 720 |
| tcagaggtgt tcttctactt ggcacagaac aacgtcatgt ttgagggcat tctgttgaag | 780 |
| ccgagcatgg tcaccccagg cgctgagcac aagaacaagg cctctcccga ccgttgca | 840 |
| gatttcacgc tcaccatgct gaaaaggagg gttcctccgg ctgtcccagg atcatgtttt | 900 |
| ctgtcaggag gacaatcaga ggcagaggcc acactgaacc tgaacgccat gaaccagagc | 960 |
| ccaaacccat ggcatgtgtc cttctcatac gcacgtgccc tgcagaactc cgtgctcaga | 1020 |
| acatggcaag gcaagccgga gaagattgag gcctcgcaga aggcactgtt ggtgagggca | 1080 |
| aaggccaact cactggccca gctcggcaaa tactcagccg agggagagaa cgaggatgcc | 1140 |
| aagaaaggaa tgtttgtcaa gggttacacc tactga | 1176 |

<210> SEQ ID NO 3
<211> LENGTH: 1515
<212> TYPE: DNA
<213> ORGANISM: Arabidopsis thaliana

<400> SEQUENCE: 3

| | | | |
|---|---|---|---|
| ccaaagtaga cgactactaa tagtagtaaa caaaacccttt ggctttaaca ctctcctcca | 60 |
| aatcccagat ctctctctgt ctctgtcccg cggagtcccc gagagattga tcaccatcac | 120 |
| ttttgtacct tccttgtact acctatggcg tctgctagct tcgttaagcc taacaccctc | 180 |
| tcttctccat ggatcggcca acgctccttt gctcacacct ctgcttcttc ttctcctcct | 240 |
| cctcgagtct ccttcgcgat ccgcgccggt gcttactccg acgagcttgt taaaaccgcc | 300 |
| aaaagcattg catcccctgg gagaggtatc ttggcgatcg atgagtccaa tgcaacctgt | 360 |
| gggaagaggc ttgcttctat cggcttggat aacaccgagg acaaccgtca ggcctacagg | 420 |
| caacttctgc ttaccactcc tggcctcggc gattacatct ctggttccat tctcttcgag | 480 |
| gagactcttt accagtccac caaggacggt aagaccttttg tcgattgctt gcgcgatgcc | 540 |

-continued

```
aacatcgtcc ctggcatcaa agttgacaag ggcttgtctc ccctagccgg ttccaacgaa    600
gagtcttggt gccaaggctt ggatggattg gcctcacgct ctgctgagta ctacaagcaa    660
ggcgctcgtt ttgccaagtg gaggacagtg gtgagtgttc cctgcggtcc ttcagcactg    720
gctgtgaagg aagctgcgtg ggggctggct cgctatgcag ccatctctca ggataatggt    780
cttgtcccca ttgtggagcc agagatcctt ctggacgggg accacccaat agagaggact    840
ctggaggtgg cagagaaagt gtggtcagag gtgttcttct acttggcaca gaacaacgtc    900
atgtttgagg gcattctgtt gaagccgagc atggtcaccc caggcgctga gcacaagaac    960
aaggcctctc ccgagaccgt tgcagatttc acgctcacca tgctgaaaag gagggttcct   1020
ccggctgtcc cagggatcat gtttctgtca ggaggacaat cagaggcaga ggccacactg   1080
aacctgaacg ccatgaacca gagcccaaac ccatggcatg tgtccttctc atacgcacgt   1140
gccctgcaga actccgtgct cagaacatgg caaggcaagc cggagaagat tgaggcctcg   1200
cagaaggcac tgttggtgag ggcaaaggcc aactcactgg cccagctcgg caaatactca   1260
gccgagggag agaacgagga tgccaagaaa ggaatgtttg tcaagggtta cacctactga   1320
tttgttaatt tcagagatcg taataaggat taaggaccat tgttgtcttt tgttttttt    1380 tccctttttt gttttgtctc tgagaaagaa agacagtcac gagtcacgat catatcatat   1440
atgtatgtga gcaacgtgaa aacatcctct taaatctata tttcctctca gaaagactga   1500
ttactgtttg actgc                                                    1515
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4

```
ggatcctatg gcgtctgcta g                                               21
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5

```
atctgcaacg gtctcgggag a                                               21
```

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6

```
gtgtggtccg aggtgttctt ct                                              22
```

<210> SEQ ID NO 7
<211> LENGTH: 24
<212> TYPE: DNA
<213> ORGANISM: Artificial Sequence
<220> FEATURE:

-continued

<223> OTHER INFORMATION: Description of Artificial Sequence:Artificially
      Synthesized Primer Sequence

<400> SEQUENCE: 7
gagctcgagt aggtgtaacc cttg                                          24

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
ccgctgagca ataactagc                                                19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
atttaggtga cactatagaa t                                             21

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
tcactatagg gcgaattggt accga                                         25

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
aatgcaaccg ctgggaagag g                                             21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
tttgtcgatg ccttgcgcga tg                                            22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
gtcttgggcc caaggcttgg                                          20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
agtgttcccg ccggtccttc a                                        21

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
tctgctagct tggttaagcc taac                                     24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
ggcatcgcgc aagcaatcga caaa                                     24

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 17
gtccagtgtc tgtgatattg cac                                      23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 18
gcttacgaat ccgagggtgc                                          20

<210> SEQ ID NO 19
<211> LENGTH: 23
<212> TYPE: DNA
<213> ORGANISM: Artificial Sequence
<220> FEATURE:

<223> OTHER INFORMATION: Description of Artificial Sequence:Artificially
      Synthesized Primer Sequence

<400> SEQUENCE: 19
ctggtttgcc ccagcaggcg aaa                                           23

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 20
ggggaataaa atggtaaaga gaaggaggc                                     29

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 21
gcaataatca gagaatctca ctct                                          24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 22
cagccccaag actacttcaa tgc                                           23

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 23
ggtcgttcaa taagaatgac agacg                                         25

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 24
taagtttgct tccatcatca ccc                                           23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

```
<400> SEQUENCE: 25
gtgctgggaa gacatagttg cat                                                  23
```